(12) United States Patent
Sela et al.

(10) Patent No.: US 9,943,489 B2
(45) Date of Patent: Apr. 17, 2018

(54) EXTENDED RELEASE FORMULATIONS OF RASAGILINE AND USES THEREOF

(75) Inventors: Yoram Sela, Raanana (IL); Nurit Livnah, Mazkeret Batya (IL); Itschak Lamensdorf, Modiin (IL); Tomer Madmon, Kfar Yona (IL)

(73) Assignee: PHARMATWOB LTD., Rehovot (IL)

( * ) Notice: Subject to any disclaimer, the term of this patent is extended or adjusted under 35 U.S.C. 154(b) by 0 days.

(21) Appl. No.: 13/577,099

(22) PCT Filed: Feb. 3, 2011

(86) PCT No.: PCT/IL2011/000126
§ 371 (c)(1),
(2), (4) Date: Aug. 3, 2012

(87) PCT Pub. No.: WO2011/095973
PCT Pub. Date: Aug. 11, 2011

(65) Prior Publication Data
US 2012/0301542 A1    Nov. 29, 2012

Related U.S. Application Data

(60) Provisional application No. 61/301,019, filed on Feb. 3, 2010.

(51) Int. Cl.
*A61K 9/50* (2006.01)
*A61K 31/135* (2006.01)

(52) U.S. Cl.
CPC .......... *A61K 9/5078* (2013.01); *A61K 31/135* (2013.01)

(58) Field of Classification Search
None
See application file for complete search history.

(56) References Cited

U.S. PATENT DOCUMENTS

| | | | | |
|---|---|---|---|---|
| 4,415,547 A | * | 11/1983 | Yu et al. ................... | 424/469 |
| 5,496,561 A | * | 3/1996 | Okada et al. ............. | 424/480 |
| 2004/0127577 A1 | * | 7/2004 | Blaugrund et al. ....... | 514/657 |
| 2006/0018957 A1 | * | 1/2006 | Lerner et al. ............. | 424/451 |
| 2011/0230513 A1 | | 9/2011 | Lamensdorf et al. | |

FOREIGN PATENT DOCUMENTS

| CN | 101486655 A | 7/2009 |
|---|---|---|
| EP | 2218444 A2 | 8/2010 |
| WO | 199511016 A1 | 4/1995 |
| WO | 2006014973 A2 | 2/2006 |
| WO | 2009151594 A1 | 12/2009 |

OTHER PUBLICATIONS

Lecomte et al. (Journal of Controlled Release 2003, 89, 457-471).*
Finberg et al., "Pharmacology of Rasagiline, a New MAO-B Inhibitor Drug for the Treatment of Parkinson's Disease with Neuroprotective Potential" Rambam Maimonides Medical Journal 1(1):1-10(2010).
Thébault et al., "Tolerability, Safety, Pharmacodynamics, and Pharmacokinetics of Rasagiline: A Potent, Selective, and Irreversible Monoamine Oxidase Type B Inhibitor" Pharmacotherapy 24(10)1295-1305 (2004).

* cited by examiner

Primary Examiner — Tigabu Kassa
(74) Attorney, Agent, or Firm — Browdy and Neimark, PLLC

(57) ABSTRACT

The present invention provides various pharmaceutical compositions, in particular for oral administration, formulated for extended release of active compounds useful in the treatment of neurodegenerative diseases, in particular Parkinson's disease, and injuries to the nervous system. The active compound comprised within these compositions is preferably selected from N-propargyl-1-aminoindan, an enantiomer thereof, or a pharmaceutically acceptable salt thereof, more preferably rasagiline or a pharmaceutically acceptable salt thereof.

25 Claims, 7 Drawing Sheets

EXTENDED RELEASE FORMULATIONS OF RASAGILINE AND USES THEREOF

TECHNICAL FIELD

The present invention relates to pharmaceutical compositions formulated for extended release of active compounds useful in the treatment of neurodegenerative diseases, in particular Parkinson's disease, and injuries to the nervous system.

BACKGROUND ART

Several propargylamine derivatives have been shown to selectively inhibit monoamine oxidase (MAO)-B and/or MAO-A activity, which inactivate monoaminergic neurotransmitters such as dopamine, and thus to be suitable for treatment of neurodegenerative diseases such as Parkinson's disease (PD) and Alzheimer's disease (AD), in which dopamine levels are low. These compounds have further been shown to protect against neurodegeneration by preventing apoptosis.

The first compound found to selectively inhibit MAO-B was R-(-)—N-methyl-N-(prop-2-ynyl)-2-aminophenylpropane, also known as L-(-)-deprenyl, R-(-)-deprenyl, or selegiline. In addition to PD, other diseases and conditions for which selegiline was disclosed as being useful include drug withdrawal (WO 92/21333, including withdrawal from psychostimulants, opiates, narcotics, and barbiturates); depression (U.S. Pat. No. 4,861,800); AD; macular degeneration (U.S. Pat. No. 5,242,950); age-dependent degeneracies, including renal function and cognitive function as evidenced by spatial learning ability (U.S. Pat. No. 5,151,449); pituitary-dependent Cushing's disease in humans and nonhumans (U.S. Pat. No. 5,192,808); immune system dysfunction in both humans (U.S. Pat. No. 5,387,615) and animals (U.S. Pat. No. 5,276,057); age-dependent weight loss in mammals (U.S. Pat. No. 5,225,446); schizophrenia (U.S. Pat. No. 5,151,419); and various neoplastic conditions including cancers, such as mammary and pituitary cancers. WO 92/17169 discloses the use of selegiline in the treatment of neuromuscular and neurodegenerative diseases and in the treatment of CNS injury due to hypoxia, hypoglycemia, ischemic stroke or trauma. In addition, the biochemical effects of selegiline on neuronal cells have been extensively studied (see, e.g., Tatton, 1993; and Tatton and Greenwood, 1991). U.S. Pat. No. 6,562,365 discloses the use of desmethylselegiline for selegiline-responsive diseases and conditions.

Rasagiline, R(+)—N-propargyl-1-aminoindan, a highly potent selective irreversible MAO-B inhibitor, has been approved for treatment of PD in Europe, Israel, and in the U.S., under the name AZILECT® or AGILECT® (Teva Pharmaceutical Industries Ltd., Petach Tikvah, Israel). Rasagiline has been shown to exhibit neuroprotective activity and antiapoptotic effects against a variety of insults in cell cultures and in vivo (Youdim and Weinstock, 2002a). The mechanism underlying the neuroprotection by rasagiline has been studied in dopaminergic SH-SY5Y and PC12 cells in culture against apoptosis induced by N-methyl (R) salsolinol, the peroxynitrite donor N-morpholino-sydnonimine (SIN-1), 6-hydroxydopamine, and serum and nerve growth factor withdrawn (Youdim et al., 2001b; Akao et al., 1999, 2002; Maruyama et al., 2001a, 2001b, 2002).

Rasagiline and pharmaceutically acceptable salts thereof were first disclosed in U.S. Pat. Nos. 5,387,612, 5,453,446, 5,457,133, 5,576,353, 5,668,181, 5,786,390, 5,891,923, and 6,630,514 as useful for the treatment of PD, memory disorders, dementia of the Alzheimer type, depression, and the hyperactive syndrome. The 4-fluoro-, 5-fluoro- and 6-fluoro-N-propargyl-1-aminoindan derivatives were disclosed in U.S. Pat. No. 5,486,541 for the same purposes. U.S. Pat. Nos. 5,519,061, 5,532,415, 5,599,991, 5,744,500, 6,277,886, 6,316,504, 5,576,353, 5,668,181, 5,786,390, 5,891,923, and 6,630,514 disclose rasagiline and pharmaceutically acceptable salts thereof as useful for treatment of additional indications, in particular, an affective illness, a neurological hypoxia or anoxia, neurodegenerative diseases, a neurotoxic injury, stroke, brain ischemia, a head trauma injury, a spinal trauma injury, schizophrenia, an attention deficit disorder, multiple sclerosis, and withdrawal symptoms.

U.S. Pat. No. 6,251,938 describes N-propargyl-phenylethylamine compounds, and U.S. Pat. Nos. 6,303,650, 6,462,222 and 6,538,025 describe N-propargyl-1-aminoindan and N-propargyl-1-aminotetralin compounds as being useful for treatment of depression, attention deficit disorder, attention deficit and hyperactivity disorder, Tourette's syndrome, AD and other dementia such as senile dementia, dementia of the Parkinson's type, vascular dementia and Lewy body dementia.

Previous work has suggested that rasagiline and related propargylamine derivatives suppress apoptotic death cascade initiating in the mitochondria, by preventing preapoptotic decline in mitochondrial membrane potential (ATM) due to permeability transition and the activation of caspase 3, nuclear translocation of glyceraldehyde-3-phosphate dehydrogenase, and nucleosomal DNA fragmentation apoptotic processes (Youdim and Weinstock, 2002b). In controlled monotherapy and as an adjunct to L-dopa, rasagiline has shown anti-Parkinson activity.

Two rasagiline analogs containing a carbamate moiety have been synthesized in an attempt to combine the MAO inhibitory and neuroprotective properties of rasagiline with the cholinesterase (ChE)-inhibiting activity of rivastigmine, a drug with proven efficacy in AD patients. These analogs are (N-propargyl-(3R)aminoindan-5-yl)-ethylmethyl carbamate (TV3326), which possesses both ChE and MAO-A and B inhibitory activities, and its S-isomer, TV3279, an inhibitor of ChE but not of MAO (Weinstock, 1999; Grossberg and Desai, 2001). Similar to rasagiline, TV3326 and TV3279 possess neuroprotective properties against a variety of insults, which are independent of the ChE and MAO inhibitory activities, but may derive from some intrinsic pharmacological activity of the propargylamine moiety (Youdim and Weinstock, 2002a). In addition, these compounds stimulate the release of the neurotrophic/neuroprotective nonamyloidogenic-soluble amyloid precursor protein (sAPPI3) via activation of the protein kinase C and mitogen-activated protein kinase pathways (Yogev-Falach, 2002). Thus, these drugs may affect the formation of potentially amyloidogenic derivatives and could be of clinical importance for treatment of AD.

U.S. Pat. No. 5,169,868, U.S. Pat. No. 5,840,979 and U.S. Pat. No. 6,251,950 disclose aliphatic propargylamines as selective MAO-B inhibitors, neuroprotective and cellular rescue agents. The lead compound, (R)—N-(2-heptyl) methyl-propargylamine, has been shown to be a potent MAO-B inhibitor and antiapoptotic agent (Durden et al., 2000).

Propargylamine was reported many years ago to be a mechanism-based inhibitor of the copper-containing bovine plasma amine oxidase (BPAO), though the potency was modest. U.S. Pat. No. 6,395,780 discloses propargylamine as a weak glycine-cleavage system inhibitor.

SUMMARY OF THE INVENTION

It has been found, in accordance with the present invention, that administration of rasagiline in a sustained release manner, following which the exposure to the drug is remarkably extended compared to that resulting from acute administration, may be critical for obtaining optimal neuroprotection against various insults to the CNS. More particularly, while acute administration of increasing doses of rasagiline (0.1, 0.12 or 0.15 mg/kg) in the N-methyl-4-phenyl-1,2,3,6-tetrahydropyridine (MPTP)-mouse model of Parkinson's disease (PD) had practically a similar effect on the dopamine levels of the mice leading to increase in dopamine content to around 60% compared to naïve mice, administration of the same three doses of the drug in a sustained release manner over a period of 24 hours led to a significant dose response where dopamine levels were 57%, 74% and 88%, respectively, compared to naïve mice, indicating a highly beneficial effect of the sustained release administration compared to the immediate release, on the dopamine levels in MPTP treated mice brains. Interestingly, similar results were obtained following sustained release administration of the rasagiline metabolite 1-aminoindan, leading to a significant restoration of dopamine levels in comparison to mice administered with the same drug dose once a day for the same time period.

As further found, using the 6-hydroxydopamine (6-OHDA) rat model of PD, a significantly improved effect in amphetamine-induced net rotation was observed in rats treated with rasagiline administered in a sustained release manner compared with those treated with the same drug by daily injections.

In one aspect, the present invention thus provides a pharmaceutical composition comprising a pharmaceutically acceptable carrier and an active agent comprising a propargylamine moiety, an aminoindan moiety, or both propargylamine and aminoindan moieties, or a pharmaceutically acceptable salt thereof, formulated for extended release of said active agent. In a preferred embodiment, the active agent comprised within the pharmaceutical composition is R(+)—N-propargyl-1-aminoindan (rasagiline), or a pharmaceutically acceptable salt thereof.

In another aspect, the present invention provides an extended-release pellet comprising:
  (i) an inert pellet core;
  (ii) a drug layer coating said pellet core, said drug layer comprising an active agent comprising a propargylamine moiety, an aminoindan moiety, or both propargylamine and aminoindan moieties, or a pharmaceutically acceptable salt thereof, optionally suitably admixed with a binder and/or a film-former polymer, and further optionally admixed with a glidant;
  (iii) optionally an isolating/protecting sub-coating layer coating said drug layer; and
  (iv) an extended-release coating layer coating said sub-coating layer, if present, or said drug layer.

In still another aspect, the present invention provides an oral pharmaceutical composition comprising extended-release pellets as defined above.

The various pharmaceutical compositions of the present invention are useful for treatment of neurodegenerative diseases, preferably Parkinson's disease, and injuries to the nervous system.

In a further aspect, the present invention thus relates to a method for treatment of a neurodegenerative disease or an injury to the nervous system in an individual in need thereof, comprising administering to said individual a pharmaceutical composition as defined above.

In yet a further aspect, the present invention relates to a method for preparing an extended release formulation of an active agent comprising a propargylamine moiety, an aminoindan moiety, or both propargylamine and aminoindan moieties, or a pharmaceutically acceptable salt thereof, said method comprising the steps of:
  (i) dissolving said active agent, optionally suitably admixed with a binder and/or a glidant, in a suitable solvent system to prepare a uniform suspension;
  (ii) applying a coat of the suspension obtained in (i) to inert pellets such as inert nonpareil seeds;
  (iii) optionally coating the active agent-loaded pellets obtained in (ii) with an insulating/protecting sub-coating layer;
  (iv) coating the pellets obtained in (ii) or (iii) with an extended-release coating layer which enables an extended release of said active agent thereby obtaining said extended release formulation; and
  (v) optionally blending the coated pellets obtained in (iv) with a suitable excipient.

DETAILED DESCRIPTION OF THE INVENTION

Figure 1:
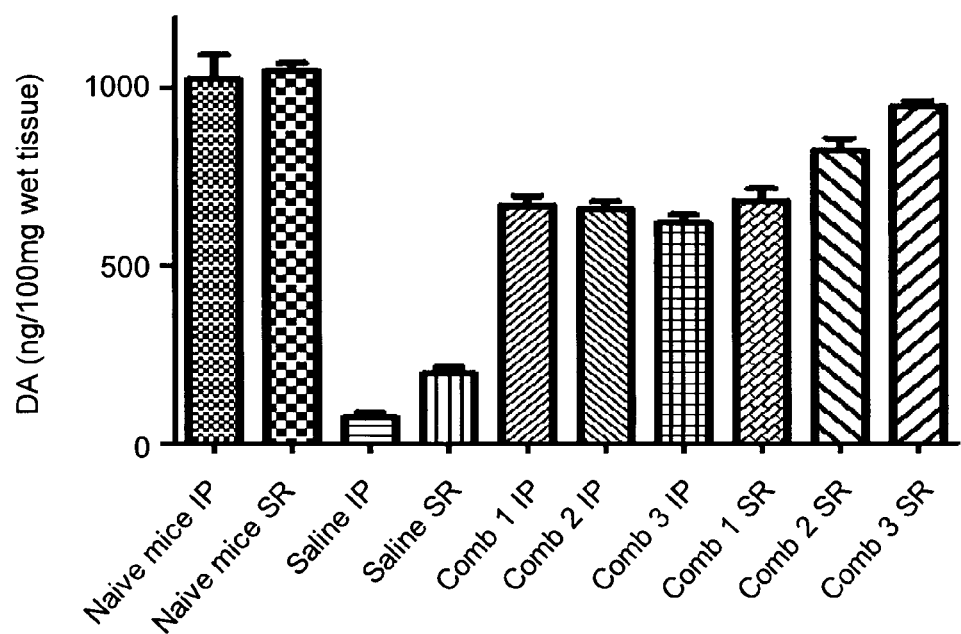
FIG. 1 shows the effect of rasagiline-pramipexole combinations (identified Comb 1, 2 and 3) in which pramipexole dose is constant (0.5 mg/kg) and rasagiline dose varies (0.1, 0.12, or 0.15 mg/kg, respectively) on brain dopamine (DA) levels. As particularly shown, MPTP administration with no drug treatment (saline IP and SR) caused over 80% depletion in dopamine levels relative to naïve mice (naïve mice IP and SR). Treatment (IP administration) with the rasagiline-pramipexole combinations caused a restoration of dopamine levels to about 60% of naïve mice, an effect that was similar in all three combinations; however, the same three combinations, when administered by sustained release (SR) using ALZET pump, led to a significant dose-response increase of 57%, 74% and 88%, in dopamine levels, in accordance with the increased doses of rasagiline.

The principal rationale for monoamine oxidase B (MAO-B) inhibition in Parkinson's disease is enhancement of striatal dopamine activity, which results in symptomatic motor benefits. Since MAO-B is responsible, inter alia, for dopamine hydrolysis, MAO-B inhibition increases the level of dopamine. According to the described mechanism of action, the activity of rasagiline is detached from its pharmacokinetics, due to the fact that MAO-B inhibition by rasagiline is irreversible and the effect resulting from that inhibition thus remains until new MAO-B is produced, i.e., for about 2-3 weeks. Therefore, it may be assumed that there should be no benefit from administration of rasagiline in a sustained release manner. Nevertheless, recent evidence indicates that rasagiline may induce neuroprotection in an alternative mechanism, through inhibition of apoptosis or other pathways. It is further known that rasagiline undergoes considerable metabolism and its major metabolite, 1-aminoindan, has neuroprotective activity that is not associated with MAO-B inhibition (Bar-Am et al., 2007; Weinreb et al., 2010).

Rasagiline, selegiline and other structurally related propargylamine derivatives increase neuronal survival independently of MAO-B inhibition, in part by decreasing apoptosis (Tatton et al., 2002). This effect is most likely modulated by altering the levels or subcellular localization of proteins that affect mitochondrial membrane permeability, scavenge oxidative radicals, or participate in specific apoptosis signaling pathways. Both rasagiline and selegiline, as well as other propargylamine derivatives, have been confirmed to protect neurons against cell death induced by various insults in cellular and animal models of neurodegenerative disorders such as Parkinson's disease and Alzheimer's disease. The propargylamine chain confers dose-related antioxidant and antiapoptotic effects, which have been associated with neuroprotection in multiple experimental models. According to recent publications, the neuroprotective effect of rasagiline may be associated with the combination of rasaligine and its metabolite 1-aminoindan (Tazik et al., 2009; Bar-Am, 2010).

In one aspect, the present invention provides a pharmaceutical composition comprising a pharmaceutically acceptable carrier and an active agent comprising a propargylamine moiety, an aminoindan moiety, or both propargylamine and aminoindan moieties, or a pharmaceutically acceptable salt thereof, formulated for extended release of said active agent.

The concept underlying the present invention is based on the findings shown in the Examples section hereinafter. Example 1 shows that while acute administration of increasing doses of rasagiline (0.1, 0.12 or 0.15 mg/kg) in the MPTP-mouse model of PD had practically a similar effect on the dopamine levels of the mice leading to increase in dopamine content to around 60% compared to naïve (MPTP-treated) mice, administration of the same three doses of rasagiline in a sustained release manner over a period of 24 hours led to a significant dose response where dopamine levels were 57%, 74% and 88%, respectively, compared to naïve mice, indicating a highly beneficial effect of the sustained release administration compared to the immediate release, on the dopamine levels in MPTP treated mice brains. Example 2 describes a study utilizing the same mice model of PD, in which mice were treated with the rasagiline metabolite 1-aminoindan, and shows that treatment with 1-aminoindan administrated in a sustained release manner causes a significant restoration of dopamine levels, in comparison to vehicle (saline) treated mice or the same drug administrated by daily injections. These findings are further supported by the study described in Example 3, showing that in the 6-OHDA rat model of PD, a remarkably improved effect in amphetamine-induced net rotation (CW-CCW) is observed in rats treated with rasagiline administered in a sustained release manner compared with those treated with the same drug by daily injections.

As in fact shown herein for the first time, when rasagiline is being delivered in an extended release manner, the exposure to the drug or to its active metabolite 1-aminoindan is significantly extended thereby enabling much more effective neuroprotection that may remarkably improve the patient's condition. According to this concept, both rasagiline and selegiline that are MAO-B inhibitors indicated for treatment of Parkinson's disease, as well as other propargylamine derivatives, can be considered as "prodrugs" continuously releasing the active agent or as propagylamine/aminoindan "delivery vehicles". These prodrugs or delivery vehicles, independently of their MAO inhibition activity, protects neuronal cells throughout different stages of the apoptotic process by the means of the chronic sustained exposure to an active agent as defined above, i.e., an active agent comprising a propargylamine moiety, an aminoindan moiety, or both propargylamine and aminoindan moieties, or a pharmaceutically acceptable salt thereof.

According to the present invention, any pharmaceutically acceptable salt of the active agent can be used. Examples of pharmaceutically acceptable salts include, without being limited to, the mesylate salt, the esylate salt, the tosylate salt, the sulfate salt, the sulfonate salt, the phosphate salt, the carboxylate salt, the maleate salt, the fumarate salt, the tartrate salt, the benzoate salt, the acetate salt, the hydrochloride salt, and the hydrobromide salt.

In certain embodiments, the active agent comprised within the pharmaceutical composition of the present invention is N-propargyl-1-aminoindan, an enantiomer thereof, a metabolite thereof, an analog thereof, or a pharmaceutically acceptable salt of any of the aforesaid.

In one particular embodiment, the active agent is N-propargyl-1-aminoindan in its racemic form as described, e.g., in U.S. Pat. No. 6,630,514, or a pharmaceutically acceptable salt thereof.

In other particular embodiments, the active agent is R(+)—N-propargyl-1-aminoindan (rasagiline), its S-enantiomer S-(−)—N-propargyl-1-aminoindan, or a pharmaceutically acceptable salt thereof. In more particular embodiments, the active agent is the mesylate salt, the esylate salt, the tosylate salt, the sulfate salt, the sulfonate salt, the phosphate salt, the carboxylate salt, the maleate salt, the fumarate salt, the tartrate salt, the benzoate salt, the acetate salt, the hydrochloride salt, or the hydrobromide salt of either rasagiline or S-(−)—N-propargyl-1-aminoindan. In preferred embodiments, the active agent is rasagiline mesylate, described, e.g., in U.S. Pat. No. 5,532,415; rasagiline esylate or rasagiline sulfate, described, e.g., in U.S. Pat. No. 5,599,991; or rasagiline hydrochloride, described, e.g., in U.S. Pat. No. 6,630,514, more preferably, rasagiline mesylate.

In a further particular embodiment, the active agent is the rasagiline metabolite 1-aminoindan, or a pharmaceutically acceptable salt thereof.

In still other particular embodiments, the active agent is an analog of N-propargyl-1-aminoindan, an enantiomer thereof, or a pharmaceutically acceptable salt thereof. Examples of such analogs include the compounds described in U.S. Pat. No. 5,486,541 such as, but not limited to, 4-fluoro-N-propargyl-1-aminoindan, 5-fluoro-N-propargyl-1-amino indan, and 6-fluoro-N-propargyl-1-aminoindan; the compounds described in U.S. Pat. No. 6,251,938 such as, but not limited to, 3-(N-methyl,N-propyl-carbamyloxy)-α-methyl-N'-propargyl phenethylamine; 3-(N,N-dimethyl-carbamyloxy)-α-methyl-N'-methyl, N'-propargyl phenethylamine; 3-(N-methyl,N-hexyl-carbamyloxy)-α-methyl-N'-methyl,N'-propargyl phenethylamine; 3-(N-methyl,N-cyclohexyl-carbamyloxy)-α-methyl-N'-methyl,N'-propargyl phenethyl amine; and 3-(N-methyl,N-hexyl-carbamyloxy)-α-methyl-N'-methyl, N'-propargyl phenethylamine; compounds described in U.S. Pat. No. 6,303,650 such as, but not limited to, 6-(N-methyl,N-ethyl-carbamyloxy)-N'-propargyl-1-amino indan; 6-(N,N-dimethyl-carbamyloxy)-N'-methyl-N '-propargyl-1-amino indan; 6-(N-methyl,N-ethyl-carbamyloxy-N'-propargyl-1-aminotetralin; 6-(N,N-dimethyl-thiocarbamyloxy)-1-aminoindan; 6-(N-propyl-carbamyloxy)-N'-propargyl-1-aminoindan; 5-chloro-6-(N-methyl,N-propyl-carbamyloxy)-N'-propargyl-1-aminoindan; and 6-(N-methyl), N-propyl-carbamyloxy)-N'-propargyl-1-aminoindan; and the compounds described in U.S. Pat. No. 6,462,222 such as, but not limited to, 6-(N-methyl,N-ethyl-carbamyloxy)-N'-methyl, N'-propargyl-1-aminoindan.

In other certain embodiments, the active agent comprised within the pharmaceutical composition of the present invention is propargylamine, an aliphatic propargylamine, or a pharmaceutically acceptable salt thereof.

In one particular embodiment, the active agent is propargylamine, or a pharmaceutically acceptable salt thereof.

In other particular embodiments, the active agent is an aliphatic propargylamine described in U.S. Pat. No. 5,169,868, U.S. Pat. No. 5,840,979 or U.S. Pat. No. 6,251,950 such as, without being limited to, N-(1-heptyl)propargylamine; N-(1-octyl)propargylamine; N-(1-nonyl)propargylamine; N-(1-decyl)propargylamine; N-(1-undecyl)propargylamine; N-(1-dodecyl)propargylamine; N-(2-butyl)propargylamine; N-(2-pentyl)propargylamine; N-(2-hexyl)propargylamine; N-(2-heptyl)propargylamine; N-(2-octyl)propargylamine; N-(2-nonyl)propargylamine; N-(2-decyl)propargylamine; N-(2-undecyl)propargylamine; N-(2-dodecyl)propargylamine; N-(1-butyl)-N-methylpropargylamine; N-(2-butyl)-N-methylpropargylamine; N-(2-pentyl)-N-methylpropargylamine; (1-pentyl)-N-methylpropargylamine; N-(2-hexyl)-N-methyl propargylamine; (2-heptyl)-N-methylpropargylamine; N-(2-decyl)-N-methyl propargylamine; (2-dodecyl)-N-methylpropargylamine; an enantiomer thereof; or a pharmaceutically acceptable salt thereof.

In further certain embodiments, the active agent comprised within the pharmaceutical composition of the present invention is selegiline, desmethylselegiline, pargyline, or chlorgyline.

In yet a further certain embodiment, the active agent comprised within the pharmaceutical composition of the present invention is (N-methyl-N-propargyl)-10-aminomethyl-dibenzo[b,f]oxepin, also known as CGP 3466 and described in Zimmermann et al. (1999).

All the US patents and other publications mentioned hereinabove are hereby incorporated by reference in their entirety as if fully disclosed herein.

The term "extended release", "controlled release" or "sustained release", as used herein interchangeably, refers to a mode of releasing an active agent from the formulation thereof such that it is absorbed by the body over a period of time. An extended release formulation of an active agent may be accomplished, e.g., by embedding the active agent in a web of substance that the body is slow to dissolve, such that the active ingredient slowly and regularly leeches from the coating, or by swelling up the active agent to form a gel with a nearly impenetrable surface, wherein the drug slowly exits the semipermeable layer.

Major principles in the development of a controlled release product are substance release at the intended site (targeting); at a constant rate; and within the required therapeutic window. Mechanisms based on the principle of Solvent Controlled System, such as swelling and osmosis systems, which maintain a constant concentration of active substance in the blood for long periods of time, achieve more effective drug levels with less side effects. In other words, the therapeutic window is the dosage of a medication between the amount that gives an effect (effective dose) and the amount that gives more adverse effects than desired effects. To that extent, the dissolution profile of each drug should be designed according to the individual bioavailability, action site and absorption properties of each compound.

The pharmaceutical composition of the invention should provide for controlled release of the drug, i.e., the active agent. In certain embodiments, the drug is released from the pharmaceutical composition in a controlled release manner of zero, first, second or any other release profile ($N^{th}$ order). The controlled release of the drug should preferably be slow and in certain embodiments the pharmaceutical composition is formulated so as to provide continuous sustained drug release, pulsatile drug release, multiphase drug release, or a combination thereof.

The pharmaceutical compositions of the present invention may be prepared by conventional techniques, e.g., as described in Remington: The Science and Practice of Pharmacy, $19^{th}$ Ed., 1995, may appear in any conventional form, and may be provided in a variety of dosages.

The compositions can be formulated for any suitable route of administration, e.g., intravenous, intraarterial, intramuscular, subcutaneous or intraperitoneal administration, but they are preferably formulated for oral administration.

The dosage will depend on the state of the patient, and will be determined as deemed appropriate by the practitioner. In particular embodiments, the dosage is 0.1-2.0, preferably 0.2-1.5, more preferably 0.5-1.0, mg per day for a 60 kg adult. The compositions of the invention may be administered, e.g., continuously, daily, twice daily, thrice daily or four times daily, for various duration periods, e.g., weeks, months, years, or decades.

The pharmaceutical composition of the invention may be, e.g., in the form of a sterile injectable aqueous or oleagenous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution and isotonic sodium chloride solution.

Pharmaceutical compositions according to the invention, when formulated for oral administration may be in a form of tablets, troches, lozenges, aqueous, or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active agent in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binders; and lubricating agents. The tablets are preferably coated utilizing known techniques to delay disintegration and absorption in the gastrointestinal tract and thereby provide an extended release of the drug over a longer period. For example, a time delay material such as glyceryl monostearate or glyceryl distearate may be employed. They may also be coated using the techniques described in the U.S. Pat. Nos. 4,256,108, 4,166,452 and 4,265,874 to form osmotic therapeutic tablets for control release. The pharmaceutical composition of the invention may also be in the form of bilayer tables, in which two or more distinct layers of granulation compressed together with the individual layers lying one on top of another, with each separate layer formulated to provide a different mode of release of the drug. Oral pharmaceutical composition of the invention may also be in the form of oil-in-water emulsion.

The pharmaceutical compositions of the invention may also be formulated as controlled-release matrix, e.g., as controlled-release matrix tablets in which the release of a soluble active agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or hydroxypropyl methyl cellulose, and among the different commercial grades of these ethers are those showing fairly high viscosity. In other configurations, the compositions comprise the active agent formulated for controlled release in microencapsulated dosage form, in which small droplets of the active agent are surrounded by a coating or a membrane to form particles in the range of a few micrometers to a few millimeters.

Another contemplated formulation is depot systems, based on biodegradable polymers, wherein as the polymer degrades, the active agent is slowly released. The most common class of biodegradable polymers is the hydrolytically labile polyesters prepared from lactic acid, glycolic acid, or combinations thereof.

The pharmaceutical composition of the invention may comprise one or more pharmaceutically acceptable excipients. For example, a tablet may comprise at least one filler, e.g., lactose, ethylcellulose, microcrystalline cellulose, silicified microcrystalline cellulose; at least one disintegrant, e.g., cross-linked polyvinylpyrrolidinone; at least one binder, e.g., polyvinylpyridone, hydroxypropylmethyl cellulose; at least one surfactant, e.g., sodium laurylsulfate; at least one glidant, e.g., colloidal silicon dioxide; and at least one lubricant, e.g., magnesium stearate.

Examples 4-6 hereinafter describe the preparation of three types of rasagiline mesylate extended release (ER) coated pellets comprising a drug layer coating inert pellets and an extended release, i.e., functional, layer coating the drug layer (15%, 22% and 28% ER layer). For the preparation of the drug layer, povidone USP (PVP K29/32) was dissolved in distilled water and ethanol mixture; the drug was dissolved in the formed solution; and talc extra fine was then dispersed and added to the solution to form a uniform suspension, which was coated on sugar spheres 600-710 μm (diameter). For the preparation of the various thickness ER coating films, one solution was prepared, from which samples were taken at different time points during the coating process, corresponding to different amounts of sprayed solution leading to varying layer thickness. The solution consisted of Ethocel 45 cps (ethylcellulose; a release control polymer) dissolved in acetone and ethanol mixture; and polyethylene glycol (PEG) 4000 dissolved in distilled water, which were then mixed together to form a homogeneous solution. The functional solution was coated on the drug-loaded pellets as described above, to form various thickness ER films. Dissolution profiles of the various ER coated pellets were evaluated in USP (United States Pharmacopeia) Apparatus 1 (basket) at a spindle rotation speed of 100 rpm and a temperature of 37° C., using intestinal fluid solution (IFS, pH 6.8), mimicking the conditions in the intestines, and as shown, the release rate was influenced by the film thickness and had slower release pattern as the functional layer being thicker.

Examples 7-8 describe the preparation of two types of rasagiline mesylate ER coated pellets comprising a drug layer coating inert pellets, a sub-coating layer coating said drug layer, and a functional layer coating the sub-coating layer (15% and 18% ER layer). For the preparation of the drug layer, povidone (PVP K25) was dissolved in distilled water and ethanol mixture; the drug was dissolved in the formed solution; and talc extra fine was then dispersed and added to the formed solution to form a uniform suspension, which was then coated on sugar spheres 600-710 μm. The sub-coating solution was prepared by dissolving PVP K25 in distilled water and ethanol mixture, and was then coated on the drug-loaded pellets. For the preparation of the various thickness ER coating films, one solution was prepared, from which samples were taken at different time points during the coating process, corresponding to different amounts of sprayed solution leading to varying layer thickness. The solution consisted of Ethocel 45 cps dissolved in acetone and ethanol mixture; and PEG 3000 dissolved in distilled water, which were then mixed together to form a homogeneous solution. Talc extra fine was dispersed in distilled water and added to the solution to form a uniform suspension, which was then coated on the sub coated pellets to form various thickness ER films. The obtained pellets were then dry mixed with Aerosil 200. Dissolution profiles of these two ER coated pellets were evaluated in USP Apparatus 1 at 100 rpm and a temperature of 37° C., using (i) IFS (pH 6.8), mimicking the conditions in the intestines; (ii) gastric fluid solution (GFS, pH 1.2), mimicking the conditions in an empty stomach, for 2 hours, and then in IFS for additional 20 hours; and (iii) acetate buffer (pH 4.5), mimicking the conditions in a full stomach, and as shown, the release rate remained constant (within the acceptable range of ±10% for dissolution test) at the range of pH 1.2-6.8 due to the pH independent polymers in the ER layer, and remained stable for 3 months despite exposure to stability-accelerated conditions. The release rate from the 15% ER coated pellets was faster than that from the 18% ER coated pellets due to the differences in the functional layer thickness.

Example 9 describes the preparation of a third type of rasagiline mesylate ER coated pellets comprising a drug layer coating inert pellets, a sub-coating layer, and an outer functional layer having a higher percentage (27%) of an ER coating layer, which were dry mixed with silicon dioxide instead of Aerosil 200 used in Examples 7-8. The dissolution profile of these pellets was evaluated in USP Apparatus 1 at 100 rpm and a temperature of 37° C., using IFS (pH 6.8), and as shown, the release pattern in this case was slower than that observed for the pellets of Examples 7-8 due to the differences in the functional layer thickness.

Additional rasagiline mesylate ER pellets with or without sub-coating layer, designed for different releasing profiles of the drug, are described in Example 10.

When designing a 24-hours extended release product for oral administration, it is necessary that the drug be absorbed throughout the entire releasing time, i.e., from all the parts of the gastrointestinal track, including both the duodenum and the colon. Example 11 describes a pharmacokinetic study, in which a single bolus dose of rasagiline was administrated as an aqueous solution to the colon, duodenum or jugular vein of rats, blood samples were taken from the animals at 5 minutes pre-dose, and 5, 15, 30, 50, 90, 150 and 200 minutes post-dose, and plasma levels of both rasagiline and its metabolite were measured. As shown, parent $T_{1/2}$ for the colonic and duodenal administration groups was longer compared to $T_{1/2}$ after IV administration. In addition, similar area under curve (AUC) values were calculated for the IV and duodenal dose suggesting a complete oral absorption, while the AUC value after colonic administration was approximately 28% of the IV dose AUC value, proving the feasibility of colonic absorption.

In view of the dissolution profiles provided for the various rasagiline mesylate ER coated pellets described above, and the study described hereinabove showing absorption of rasagiline from various parts of the gastrointestinal track, in certain embodiments, the pharmaceutical composition of the present invention is formulated for oral administration. In particular embodiments, the pharmaceutical composition may be solid in the form of granules, grains, beads or pellets, which are mixed and filled into capsules or sachets or are compressed to tablets by any conventional method known in the art, as shown with respect to some of the rasagiline mesylate ER pellets described in Example 10. For example, there is provided a tablet in which the active agent is present in at least two separate layers, i.e., a bilayer or multilayer tablet, wherein the layers are optionally separated by an intermediate, inactive layer, e.g., a layer comprising one or more disintegrants. The pharmaceutical composition may also be a semi-solid or liquid system.

In certain embodiments, the pharmaceutical composition of the invention, when formulated for oral administration, is in the form of a monolithic matrix, i.e., a structure including a three-dimensionally stable matrix material having a discrete size and shape; a tablet such as a bi-layered or multilayered tablet, matrix tablet, disintegrating tablet, dissolving tablet, or chewable tablet; or a capsule or sachet, e.g., filled with granules, grains, beads, or pellets. In other certain embodiments, the pharmaceutical composition of the invention, when formulated for oral administration, is in the form of a depot system, based on biodegradable polymers, wherein as the polymer degrades, the active agent is slowly released. The most common class of biodegradable polymers is the hydrolytically labile polyesters prepared from lactic acid, glycolic acid, or combinations thereof. Examples for biodegradable polymers prepared from these particular monomers include, without being limited to, poly(D,L-lactide) (PLA), polyglycolide (polyglycolic acid; PGA), and the copolymer poly(D,L-lactide-co-glycolide) (PLGA).

In certain particular embodiments, the present invention provides a pharmaceutical composition as defined above, i.e., a pharmaceutical composition comprising an active agent comprising a propargylamine moiety, an aminoindan moiety, or both propargylamine and aminoindan moieties, or a pharmaceutically acceptable salt thereof, said composition having the following dissolution profile in USP Apparatus 1 (basket) at 50-150, preferably 100, rpm in pH value of up to 7.4, preferably 1.2-6.8, at 37° C.:

| Time (hours) | Average % active agent released |
| --- | --- |
| 2 | <30 |
| 6 | 30-70 |
| 12 | 50-85 |
| 24 | >70 |

Preferred pharmaceutical compositions are those having the following dissolution profile in USP Apparatus 1 (basket) at 50-150, preferably 100, rpm in pH value of up to 7.4, preferably 1.2-6.8, at 37° C.:

| Time (hours) | Preferred average % active agent released |
| --- | --- |
| 2 | <30 |
| 6 | 30-60 |
| 12 | 50-70 |
| 24 | >70 |

In more particular embodiments, the active agent comprised within this composition is N-propargyl-1-aminoindan; an enantiomer thereof, i.e., rasagiline or S-(−)—N-propargyl-1-aminoindan; a metabolite thereof, more particularly 1-aminoindan; an analog thereof, or a pharmaceutically acceptable salt of any of the aforesaid. In most particular embodiments, the active agent comprised within this composition is rasagiline, or a pharmaceutically acceptable salt thereof.

In certain embodiments, the pharmaceutical compositions of the invention, upon administration, provide lower Cmax and smaller index of fluctuation, and lead to less unwanted side effects as compared to an immediate release dosage form. The term "Cmax", as used herein, reefers to the maximum plasma concentration of a therapeutic drug; and the term "index of fluctuation" as used herein, refers to the variations in serum concentration of a therapeutic drug as a function of time following administration of the drug. Unwanted side effects of rasagiline include, but are not limited to, severe allergic reactions (rash; hives; itching;

difficulty breathing; tightness in the chest; swelling of the mouth, face, lips, or tongue); black or bloody stools; blood in the urine; blurred vision; changes in sexual ability or desire; chest pain; confusion; depression; enlarged pupils; fast or irregular heartbeat; fever; hallucinations; inability to sit still; numbness or tingling of the hands or feet; one-sided weakness; seizures; sensitivity to light; severe headache; skin changes; sore or stiff neck; tremor; trouble thinking or walking; unexplained nausea or vomiting; unusual sweating; vision or speech problems; diarrhea; dizziness; drowsiness; dry mouth; flu-like symptoms; headache; joint pain; light-headedness; sleeplessness; stomach upset; and stuffy nose.

In another aspect, the present invention provides an extended-release (ER) pellet comprising:
(i) an inert pellet core;
(ii) a drug layer coating said pellet core, said drug layer comprising an active agent comprising a propargylamine moiety, an aminoindan moiety, or both propargylamine and aminoindan moieties, or a pharmaceutically acceptable salt thereof, optionally suitably admixed with a binder and/or a film-former polymer, and further optionally admixed with a glidant;
(iii) optionally an isolating/protecting sub-coating layer coating said drug layer; and
(iv) an extended-release coating layer coating said sub-coating layer, if present, or said drug layer.

The ER pellet of the present invention may optionally comprise an isolating/protecting sub-coating layer coating said drug layer. The role of this sub-coating layer is isolating the active material layer from the external ER coating and protecting from possible interactions with the active agent that might affect its stability and lead to formation of active pharmaceutical ingredient (API) degradation products. In certain embodiments, the sub-coating layer comprises a film-former polymer and optionally a glidant.

The ER pellet of the present invention comprises an outer ER coating layer, also termed herein "a functional layer", coating either the sub-coating layer, if present, or the drug layer.

In certain embodiments, the ER coating layer comprises at least one pH-independent polymer, i.e., a water swelling/water insoluble/hydrophobic polymer, and optionally a pore-forming agent, wherein the extended-release pellet has a pH-independent in vitro release characteristic. In other embodiments, the functional layer comprises a pH-independent polymer, a hydrophilic release modulator polymer acting as a pore-forming agent, and optionally a hydrophobic or hydrophilic plasticizer, and/or glidant. In further certain embodiments, the ER coating layer comprises a mixture of a pH-dependent enteric-coating polymer and a pH-independent polymer, wherein the extended-release pellet has a close to zero order in vitro release characteristic at either acidic or physiological pH, i.e., at pH values of up to 7.4.

Binders for pharmaceutical use are hydrophilic substances, such as sugars and polymers of natural and synthetic origin, used in the manufacture of solid dosage forms due to their adhesive and cohesive properties. The role of binders is to assist size enlargement by adding cohesiveness to powders, thereby providing granules and tablets with the necessary bonding strength. Although binders improve the appearance, hardness and friability of these preparations, they are not intended to influence the disintegration or dissolution rates of the active substances. Binders of natural origin, which have been commonly used in the past, include acacia, gelatin, starch, and hydrolyzed starch. Those substances have been replaced by binders of synthetic origin, the most important of which are povidone and various cellulose derivatives. Examples of binders that can be admixed with the active agent in the drug layer coating of the ER pellet of the invention include, without being limited to, a polyvinyl pyrrolidone (PVP), hydroxypropylmethyl cellulose (HPMC), hydroxypropyl cellulose (HPC), microcrystalline cellulose, and combinations thereof. The binder may be present in an amount from about 0.5% to about 20%, preferably from about 0.5% to about 10%, by weight of the entire pellet.

The term "film-former polymer" as used herein refers to polymers capable of hardening to coherent films. In addition, the physical property of these polymers that is essential for coating is the ability to form films or certain adhesiveness to the material to be coated. Examples of film-former polymers include, without limiting, PVP, HPMC, HPC, microcrystalline cellulose, and combinations thereof. The film-former polymer when comprised within the drug layer may be present in an amount of up to 90% by weight of the entire drug layer, preferably from about 0.5% to about 20%, by weight of the entire pellet. The amount of film-former polymer in the sub-coating layer may be up to 100% by weight of the entire sub-coating layer, preferably from about 0.5% to about 10%, by weight of the entire pellet.

Glidants are typically added to pharmaceutical compositions to enhance flowability of granulations and powders by reducing friction and surface charge. In addition, they are used as anti-tack agents during the coating process. Particular glidants such as talc and glyceryl monostearate are commonly used in coating formulations as an anti tack agents, which reduce the sticking tendency at lower product temperatures. Other glidants such as silicon dioxide colloidal provide desirable flow characteristics that are exploited to improve the flow properties of dry powders in a number of processes such as tableting and capsulation, due to their small particle size and large specific surface area. Non-limiting examples of glidants include talc, particularly talc extra fine, colloidal silicon dioxide, glyceryl monostearate, and combinations thereof.

The glidant when comprised within the drug layer may be present in an amount of up to 30% by weight of the entire drug layer, preferably from about 0.5% to about 5%, by weight of the entire pellet. The amount of glidant when comprised within the sub-coating layer may be up to about 10% by weight of the entire sub-coating layer, preferably from about 0.5% to about 5%, by weight of the entire pellet.

Examples of pH-independent polymers that may be comprised within the ER pellet of the invention include, without being limited to, ethyl cellulose, Surelease® (aqueous ethylcellulose dispersion), copolymers of acrylic and methacrylic acid esters such as Eudragit® RL (poly(ethylacrylate, methylmethacrylate, trimethylammonioethyl methacrylate chloride), 1:2:0.2), Eudragit® RS (poly(ethylacrylate, methyl methacrylate, trimethylammonioethyl methacrylate chloride), 1:2:0.1), Eudragit® NE (poly(ethylacrylate, methylmethacrylate), 2:1), and combinations thereof. The pH-independent polymer may be present in an amount from about 10% to about 50%, preferably from about 10% to about 30%, by weight of the entire pellet.

Examples of pH-dependent enteric-coating polymers that may be comprised within the ER pellet of the invention include, without limiting, Eudragit® S (poly(methacrylicacid, methylmethacrylate), 1:2), Eudragit® L 55 (poly(methacrylicacid, ethylacrylate), 1:1), Kollicoat® (poly(methacrylicacid, ethylacrylate), 1:1), hydroxypropyl methylcellulose phthalate (HPMCP), alginates, carboxymethylcellulose, and combinations thereof. The pH-dependent enteric-coating polymer may be present in an amount from about 10% to about 50%, preferably from about 10% to about 30%, by weight of the entire pellet.

The term "pore-forming agent" as used herein refers to a substance that dissolves in the body environment, thus forming open pores in the matrix that increase the diffusion rate of the active agent through the coating layer. The size of the pores formed can, to some extent, be controlled by the size of the solid particulate material being used. For uniformity of pores, the particulate material can be screened through successively finer mesh sieves to produce a desired range of particle sizes. The pore-forming agent that may be comprised within the ER pellets of the invention is either inorganic or organic substance, including, e.g., polyvinylpyrrolidone (PVP), polyethylene glycol (PEG), HPMC, HPC, methylcellulose, 1,2-propylene glycol, lactose, sucrose, talc, particularly talc extra fine, and combinations thereof. The pore-forming agent may be present in an amount from about 0.1% to about 20%, preferably from about 0.1% to about 10%, by weight of the entire pellet.

The term "hydrophilic release modulator polymer" as used herein refers to a polymer that is water soluble and controls the release of the active agent. Nevertheless, in certain embodiments, the hydrophilic release modulator polymer comprised within the ER coating layer of the ER pellet of the invention acts, in fact, as a pore-forming agent. Examples of hydrophilic release modulator polymers include, without being limited to, PVP, PEG, HPMC, HPC, and combinations thereof. The hydrophilic release modulator polymer may be present in an amount from about 0.1% to about 20%, preferably from about 0.1% to about 10%, by weight of the entire pellet.

The term "plasticizer" as used herein includes any compound or combination of compounds capable of plasticizing or softening a polymer used in the ER pellet of the present invention. During manufacture of the ER coating layer, the plasticizer can lower the melting temperature or glass transition temperature (softening point temperature) of the polymer or combination of polymers used; can broaden the average molecular weight of said polymer or combination of polymers, and can further reduce the viscosity of said polymer or combination of polymers for convenient processing of the coat solution. Non-limiting examples of plasticizers include dibutyl sebacate; dibutyl phthalate; citrate esters, such as triethylcitrate, and triacetin; propylene glycol; low molecular weight poly(alkylene oxides), such as PEG, poly(propylene glycols), and poly(ethylene/propylene glycols); and combinations thereof. The plasticizers may be present in an amount from about 0.1% to about 20%, preferably from about 0.1% to about 10%, by weight of the entire pellet.

The drug layer coating of the ER pellet of the present invention may comprise any active agent as defined above, i.e., any active agent comprising a propargylamine moiety, an aminoindan moiety, or both propargylamine and aminoindan moieties, or a pharmaceutically acceptable salt thereof. In particular embodiments, the active agent is selected from N-propargyl-1-aminoindan, an enantiomer thereof, a metabolite thereof, an analog thereof, or a pharmaceutically acceptable salt thereof. In more particular embodiments, the active agent is rasagiline, or a pharmaceutically acceptable salt thereof.

The ER pellet of the present invention may comprise further inactive ingredients such as osmotic pressure/tonicity agent. Such agents are commonly used for time-controlled disintegration when a pulsatile drug delivery is required. Examples of suitable osmotic/tonicity excipients that may be used in the preparation of the ER pellet include, without being limited to, sodium chloride and mannitol. The osmotic/tonicity agent when comprised in the ER pellet may be present in an amount of up to 20%, preferably from about 0.5% to about 10%, by weight of the entire pellet.

In particular embodiment exemplified herein, the ER pellets exemplified herein comprises an inert pellet core; a drug layer comprising the active agent admixed with PVP as a film-former polymer/binder and with talc extra fine as a glidant; and an ER coating layer comprising ethylcellulose as a pH-independent polymer, and PEG as a pore-forming agent, wherein the amount of said film-former polymer/binder is up to 90% by weight of the entire drug layer, or from about 0.5% to about 20% by weight of the entire pellet; the amount of said glidant is up to 30% by weight of the entire drug layer, or from about 0.1% to about 10% by weight of the entire pellet; the amount of said pH-independent polymer is from about 50% to about 90% by weight of the entire ER coating layer, or from about 10% to about 30% by weight of the entire pellet; and the amount of said pore-forming agent is from about 1% to about 20% by weight of the entire ER coating layer, or from about 0.1% to about 10% by weight of the entire pellet.

In other particular embodiments exemplified herein, the ER pellet of the present invention comprises an inert pellet core; a drug layer comprising said active agent admixed with PVP as a film-former polymer/binder and with talc extra fine as a glidant; an isolating/protecting sub-coating layer comprising PVP as a film-former polymer; and an ER coating layer comprising ethylcellulose as a pH-independent polymer, PEG as a pore-forming agent, and talc extra fine as a glidant, wherein the amount of said film-former polymer/binder in said drug layer is up to 90% by weight of the entire drug layer, or from about 0.5% to about 20% by weight of the entire pellet; the amount of said glidant in said drug layer is up to 30% by weight of the entire drug layer, or from about 0.1% to about 10% by weight of the entire pellet; the amount of said film-former polymer in said sub-coating layer is up to 100% by weight of the entire sub-coating layer, or from about 0.5% to about 20% by weight of the entire pellet; the amount of said pH-independent polymer is from about 50% to about 90% by weight of the entire ER coating layer, or from about 10% to about 30% by weight of the entire pellet; the amount of said pore-forming agent is from about 1% to about 20% by weight of the entire ER coating layer, or from about 0.1% to about 10% by weight of the entire pellet; and the amount of said glidant in said ER coating layer is from about 0.1% to about 20% by weight of the entire ER coating layer, or from about 0.1% to about 10%, by weight of the entire pellet.

In still another aspect, the present invention provides an oral pharmaceutical composition comprising ER pellets as defined above. In certain embodiments, the ER pellets comprised within this composition are blended with one or more suitable excipients and either filled into a capsule or compressed into a tablet. The preparation of such capsules or tablets may be carried out using any suitable technology known in the art.

Examples of suitable excipients, which may be used in the preparation of the oral pharmaceutical composition include, without being limited to, silicon dioxides, as well as other glidants known in the art as defined above.

Tablets fillers fill out the size of a tablet or capsule, making it practical to produce and convenient for the consumer to use. By increasing the bulk volume, the fillers make it possible for the final product to have the proper volume for patient handling. A good filler must be inert, compatible with the other components of the formulation, non-hygroscopic, relatively cheap, compactible, and preferably tasteless or pleasant tasting. Plant cellulose (pure plant filler) is a popular filler in tablets or hard gelatin capsules. Dibasic calcium phosphate is another popular tablet filler. A range of vegetable fats and oils can be used in soft gelatin capsules. Tablet fillers include, e.g., lactose, mannitol/Parteck®, sorbitol, starch, and combinations thereof.

Disintegrant expand and dissolve when wet causing the tablet to break apart in the digestive tract, releasing the active ingredients for absorption. Disintegrant types include water uptake facilitators and tablet rupture promoters. They ensure that when the tablet is in contact with water, it rapidly breaks down into smaller fragments, facilitating dissolution. Non-limiting examples of disintegrants include crosslinked polyvinylpyrrolidone (crospovidone), sodium/calcium carboxymethyl cellulose (CMC), croscarmellose sodium hydroxypropyl cellulose low-substituted, sodium bicarbonate, starch, sodium starch glycolate, and combinations thereof.

Lubricants are added in small quantities to tablet and capsule formulations to improve certain processing characteristics. More particular, these agents prevent ingredients from clumping together and from sticking to the tablet punches or capsule-filling machine. Lubricants also ensure that tablet formation and ejection can occur with low friction between the solid and die wall. Examples of lubricants include, without limiting, glyceryl behenate, stearic acid, talc, zinc stearate, calcium stearate, and combinations thereof.

As shown in the Examples section hereinafter with particular respect to rasagiline and its metabolite 1-aminoindan, pharmaceutical compositions according to the invention are useful for treatment of Parkinson's disease, and in addition, any other neurodegenerative disease or condition, as well as injuries to the nervous system, for which an active agent as comprised within this composition has been disclosed as being useful. Such neurodegenerative diseases or conditions include, without being limited to, Alzheimer's disease; drug withdrawal, including withdrawal from psychostimulants, opiates, narcotics, and barbiturates; depression; age-dependent degeneracies, including renal function and cognitive function as evidenced by spatial learning ability; pituitary-dependent Cushing's disease in humans and nonhumans; immune system dysfunction in both humans and animals; age-dependent weight loss in mammals; schizophrenia; various neoplastic conditions including cancers such as mammary and pituitary cancers; neuromuscular and neurodegenerative disease; dementia such as senile dementia, e.g., dementia of the Parkinson's and Alzheimer's type, vascular dementia and Lewy body dementia; hyperactive syndrome; affective illness; attention deficit disorder; hyperactivity disorder; multiple sclerosis; and Tourette's syndrome. Particular injuries to the nervous system that may be treated by the pharmaceutical composition of the invention include, without limiting, CNS injury due to head trauma injury, hypoxia, anoxia, hypoglycemia, neurotoxic injury, ischemic stroke, and trauma, as well as other nerve insults where apoptotic process take place.

In a further aspect, the present invention thus relates to a method for treatment of a neurodegenerative disease or an injury to the nervous system in an individual in need thereof, comprising administering to said individual a pharmaceutical composition as defined above.

In certain embodiments, the pharmaceutical composition used in the method of the invention is formulated for oral administration. In particular embodiments, the method of the invention comprises administering an oral pharmaceutical composition formulated for extended release of an active agent as defined above, more particularly wherein the active agent is selected from N-propargyl-1-aminoindan, an enantiomer thereof, a metabolite thereof, an analog thereof, or a pharmaceutically acceptable salt thereof, preferably wherein the active agent is rasagiline, or a pharmaceutically acceptable salt thereof.

The method of the present invention can be used for treatment of any neurodegenerative disease or injury to the nervous system as defined above. In particular embodiments, the neurodegenerative disease is Parkinson's disease or Alzheimer's disease, and the injury to the nervous system is acute brain damage, such as stroke, or traumatic brain injury.

In yet a further aspect, the present invention relates to a method for preparing an extended release formulation of an active agent as defined above, i.e., an active agent comprising a propargylamine moiety, an aminoindan moiety, or both propargylamine and aminoindan moieties, or a pharmaceutically acceptable salt thereof, said method comprising the steps of:

(i) dissolving said active agent, optionally suitably admixed with a binder and/or a glidant, in a suitable solvent system to prepare a uniform suspension;

(ii) applying a coat of the suspension obtained in (i) to inert pellets such as inert nonpareil seeds;

(iii) optionally coating the active agent-loaded pellets obtained in (ii) with an insulating/protecting sub-coating layer;

(iv) coating the pellets obtained in (ii) or (iii) with an extended-release coating layer, i.e., a polymeric layer which enables an extended release of said active agent, thereby obtaining said extended release formulation; and (v) optionally blending the coated pellets obtained in (iv) with a suitable excipient.

The method described herein, for the preparation of an extended release formulation of an active agent as defined above, can be carried out using any suitable technique known in the art, e.g., as described in detail in the Examples section hereinafter. In certain embodiments, one or more of steps (ii) and (iv) of this method, as well as steps (iii) and (v) if conducted, are carried out using a fluid bed processor.

In certain embodiments, the extended release formulation prepared according to this method is further filled into capsules or compressed into tablets.

The invention will now be illustrated by the following non-limiting Examples.

EXAMPLES

Experimental

Parkinson's Disease Models

Experimental models of Parkinson's disease (PD) are needed to gain insights into the possible pathological mechanisms of the disease, and are further essential in the development and testing of new therapeutic strategies, whether pharmacological or otherwise.

MPTP Mouse Model

A significant body of biochemical data from human brain autopsy studies and those from animal models point to an ongoing process of oxidative stress in the substantia nigra which could initiate dopaminergic neurodegeneration. Although it is not known whether oxidative stress is a primary or secondary event, oxidative stress induced by the neurotoxin MPTP(N-methyl-4-phenyl-1,2,3,6-tetrahydropyridine) has been used in animal models to investigate the process of neurodegeneration with the intent to develop antioxidant neuroprotective drugs.

MPTP is converted in the brain into the positively charged molecule MPP$^+$ (1-methyl-4-phenylpyridinium) by the enzyme monoamine oxidase (MAO)-B, causing parkinsonism in primates by killing certain dopamine-producing neurons in the substantia nigra. MPP$^+$ acts by interfering with oxidative phosphorylation in mitochondria, causing depletion of ATP and cell death. It also inhibits the synthesis of catecholamines, reduces levels of dopamine and cardiac norepinephrine, and inactivates tyrosine hydroxylase.

6-OHDA Rat Model

In modeling PD, a major advance came with the introduction of the catecholamine neurotoxin 6-hydroxydopamine (6-OHDA). This molecule is transported into the cell bodies and fibers of both dopaminergic and noradrenergic neurons, and it causes degeneration of nerve terminals and can also affect cell bodies, particularly when administered to the cell body regions. 6-OHDA neurotoxicity is based on its potent inhibitory effect on the mitochondrial respiratory enzymes (chain complexes I and IV). Due to metabolic deficits of the blockade of these enzymes, the neurons can no longer exert their normal physiological functions and consequently die. Since in PD it is mainly the dopaminergic nigrostriatal pathway that is subject to degeneration, animal models have been developed in which 6-OHDA lesions of the dopaminergic system were made by unilateral injection of the toxin directly into major efferent projection of the nigrostriatal bundle.

Sample Preparation for HPLC Analysis of Dopamine and Metabolites

Striatum tissue samples were homogenized in ice in 500 µl homogenization buffer (0.1M perchloric acid, 0.02% EDTA and 1% ETOH) using OMNI Tip homogenizing kit of OMNI International (intermediate speed, 3×10 seconds with 5 seconds intervals). The homogenates were sonicated for 5 min and were then centrifuged at 15,000 rpm at 4° C. for 15 min. The supernatants were transferred into fresh tubes and dopamine content was analyzed by HPLC.

Example 1. In Vivo Study of Rasagiline-Pramipexole Combinations in MPTP Mouse Model of PD The study included 10 groups of about 7-9 mice each, which were treated according to Table 1. In particular, the mice were intraperitoneally (IP) administered with MPTP to induce the Parkinson's disease (PD) model, and treated with drug combinations containing a constant dose of pramipexole, a non-ergoline dopamine agonist indicated for treating early-stage PD, and varying doses of rasagiline. MPTP was daily injected, during the initial 5 days (days 0-4), and the drug combinations were administered on days 0-11, either IP or using ALZET pump (ALZET micro-osmotic pump, model 1002 with a rate of 0.25 µl/hr, DURECT Corporation, Cupertino, USA) to simulate sustained release. Groups 5-7 were administered with the drug combination 30 min before MPTP application, daily during the initial five days (day 0-4), and on the following days (5-11) drugs are administrated approximately at the same time each dosing day. The ALZET pump was intraperitonealy implanted 15-17 hours before first MPTP administration (groups 8-10), and the total amount of drugs applied by the pump during the dosing period was identical to that given to the IP-injected groups. Controls were naïve untreated mice injected with saline, and MPTP-administered mice injected with saline.

Body weight was measured prior to dosing and every day during the dosing, and individual body weight changes were calculated. Clinical signs were recorded twice weekly throughout the entire study. At study termination day 12, all animals were euthanatized via $CO_2$ asphyxiation. The brain was rapidly removed, placed on a refrigerated plate and dissected. The left and right striatum were removed, weighted, snap-frozen in liquid nitrogen, and stored in −70° C. until further processing. Striatum tissue samples were prepared for HPLC as described in Experimental.

TABLE 1

Group allocation

| Group* | Treatments (daily) | Route of administration |
|---|---|---|
| 1 (n = 8) | saline + saline | saline-IP |
| 2 (n = 8) | saline + ALZET pump saline | saline-IP; ALZET pump |
| 3 (n = 7) | MPTP-HCL (40 mg/kg) + saline | MPTP + saline-IP |
| 4 (n = 6) | MPTP-HCL (40 mg/kg) + ALZET pump saline | MPTP-IP; saline-ALZET pump |
| 5 (n = 5) | MPTP-HCL (40 mg/kg) + [rasagiline (0.1 mg/Kg) + pramipexole (0.5 mg/Kg)] in saline injections | MPTP + drugs-IP |
| 6 (n = 9) | MPTP-HCL (40 mg/kg) + [rasagiline (0.12 mg/Kg) + pramipexole (0.5 mg/Kg)] in saline injections | MPTP + drugs-IP |
| 7 (n = 9) | MPTP-HCL (40 mg/kg) + [rasagiline (0.15 mg/Kg) + pramipexole (0.5 mg/Kg)] in saline injections | MPTP + drugs-IP |
| 8 (n = 9) | MPTP-HCL (40 mg/kg) + [rasagiline (0.1 mg/Kg) + pramipexole (0.5 mg/Kg)] in saline in ALZET pump | MPTP-IP; drugs-ALZET pump |
| 9 (n = 8) | MPTP-HCL (40 mg/kg) + [rasagiline (0.12 mg/Kg) + pramipexole (0.5 mg/Kg)] in saline in ALZET pump | MPTP-IP; drugs-ALZET pump |
| 10 (n = 9) | MPTP-HCL (40 mg/kg) + [rasagiline (0.15 mg/Kg) + pramipexole (0.5 mg/Kg)] in saline in ALZET pump | MPTP-IP; drugs-ALZET pump |

*The number in brackets indicates the number of mice at the end of experiment

As shown in FIG. 1, when the three rasagiline+pramipexole combinations were given IP, their effect on the dopamine levels of the mice were practically identical, leading to an increase in dopamine content to around 60% compared to naïve mice. However, when the three combinations were given in a sustained release (SR) manner using ALZET pump administering the same amount over a period of 24 hours, a significant dose response was shown, where dopamine levels were increased in accordance with the increase in rasagiline doses. Since the amount of pramipexole was the same in all combinations, the effect observed must have originated from the increasing doses of rasagiline, indicating a highly beneficial effect of the sustained release administration compared to the immediate release, on the dopamine levels in MPTP-administered mice brains.

Example 2. In Vivo Study of the Rasagiline Metabolite, Aminoindan, in MPTP Mouse Model of PD Male C57B1/6 mice weighing 20+/−1 g were used in all experiments (10 mice per group). MPTP was administrated by IP injection at a dose of 40 mg/Kg per day for 5 days. Controls were naïve untreated mice injected with saline, and MPTP-treated mice injected with saline. Aminoindan was applied for 12 days either by daily IP injection or by sustained release using an ALZET pump implanted IP. The effect of the treatments was assessed by measurement of dopamine and its metabolites (dihydroxyphenylacetic acid and homovanillic acid) in left and right striatum taken from the mice at the end of the experiment. Striatum tissue samples were prepared for HPLC as described in Experimental.

Figure 2:
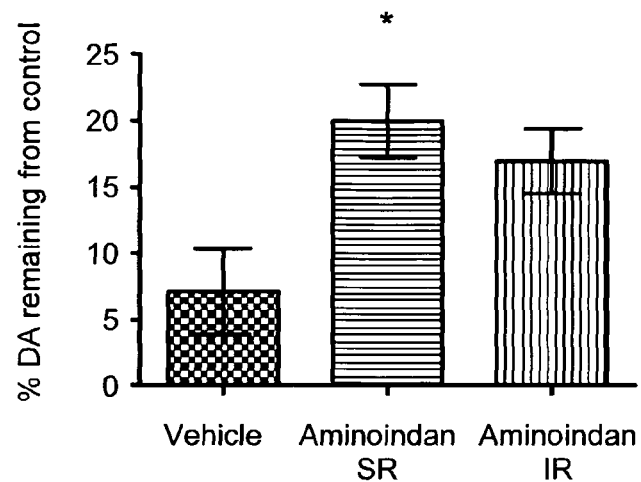
FIG. 2 shows the effect of the rasagiline metabolite, aminoindan, using SR administration on brain dopamine (DA) levels. In particular, MPTP treatment caused over 90% depletion in dopamine levels relative to naïve mice. Treatment with aminoindan administered by slow release (SR) caused a significant restoration of dopamine levels, in comparison to vehicle treated mice or aminoindan administrated by IP daily injections (IR).

As shown in FIG. 2, MPTP treatment caused over 90% depletion in dopamine levels relative to control naïve mice. Treatment with the rasagiline metabolite, aminoindan, administrated in a sustained release (SR) manner using ALZET pump caused a significant restoration of dopamine levels, in comparison to vehicle (saline) treated mice or the same drug administrated in a daily IP injection.

Example 3. In Vivo Study of Rasagiline in 6-OHDA Rat Model of PD

Unilaterally lesioning of the Medial Forebrain Bundle (MFB) by 6-OHDA causes unilaterally destruction of the dopaminergic neurons of the nigrostriatal pathway leading to asymmetry in motor behavior of rats. When lesioned rats are challenged with drugs acting on the dopamine system, they display active rotational behavior. More specifically, administration of the DA-releasing agent D-amphetamine creates a dopamine imbalance that favors the nonlesioned nigrostriatal projection and thus produces clockwise rotations. The treatment effect causes more DA to become available, and more CW rotations are expected. Drug-induced rotations are measured using an automated rotometer consisting of a rotation bowl and a swivel attached to the torso of the rat.

In addition to the results shown in Examples 1-2, indicating the clear advantage of sustained release (SR) treatment with rasagiline or its metabolite, aminoindan, on the biochemical endpoint of dopamine content in MPTP mice model of PD, in this study, the therapeutic effect of SR administration of rasagiline on behavioral endpoint was tested using the 6-OHDA rat PD model.

Male adult Sprague-Dawley rats weighing 250-300 g were lesioned with 6-OHDA in the middle forebrain bundle (MFB). Rats were anesthetized with Ketamine-Xylazine (85:15) 0.1 ml/100 g and mounted in the stereotaxic apparatus. 6-OHDA was injected into unilateral MFB according to the following stereotaxic coordinates: AP-2.8 mm, ML-2 mm relatively to the bregma, and DV-9 relatively from the Dura. The injection rate was 1 µl/min using an injection pump and Hamilton micro-syringe. After injection, the micro syringe was left for 5 min in the injection site and the hole was closed with bone wax.

Same dose of rasagiline was administered either by daily IP injections for 28 days (starting 7 days before 6-OHDA administration until 21 days after), or was applied in constant rate over 24 hours of each day, for a total of 28 days, using ALZET pump transplanted 7 days before 6-OHDA administration and continue for additional 21 days. In both cases, treatment was followed by 10 days of drug washout before rats have been sacrificed. At the end of the study, i.e., at day 32 post 6-OHDA administration, motor asymmetry was evaluated using Rota Meter with amphetamine as an inducer Amphetamine is a dopamine-releasing agent and hence depends on the number of dopaminergic (DAegic) neurons that remained viable and functional following 6-OHDA administration. Amphetamine was IP injected in a single dose of 1.5 mg/kg, followed by 60 min rotation recording on the Rota Meter.

Figure 3:
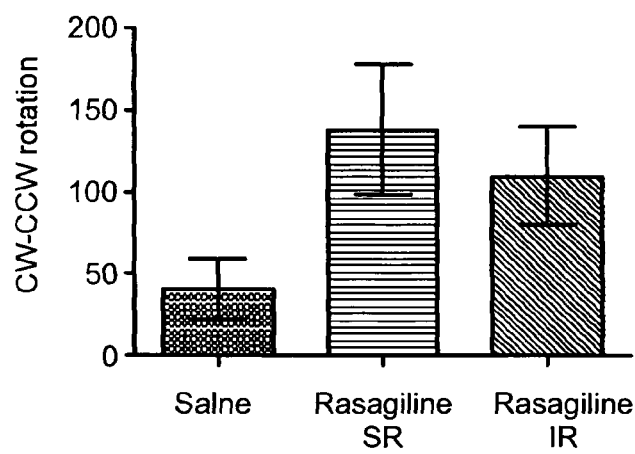
FIG. 3 shows amphetamine-induced net rotation, which is the clockwise-rotation after subtraction of counterclockwise rotation (CW-CCW) measured in rats treated with rasagiline as described in Example 3. Significant improved effect in net rotation is shown in the rats treated with sustained-released (SR) rasagiline using the ALZET pump compared with those treated with immediate-release (IR) rasagiline by IP daily injections.

As shown in FIG. 3, a significantly improved effect in net rotation, i.e., the clockwise-rotation after subtraction of counterclockwise rotation (CW-CCW), was observed in the rats that were treated with rasagiline using the ALZET pump demonstrating sustained release compared with those treated with rasagiline by IP daily injections demonstrating immediate release.

Examples 4-6. Rasagiline Extended Release Coated Pellets without Sub Coating

Rasagiline mesylate extended release (ER) pellets without sub coating having the composition shown in Table 2 were prepared. In particular, for the preparation of the drug layer, povidone USP (PVP K29/32) was dissolved in distilled water and ethanol 96% mixture, and rasagiline mesylate was then dissolved in the formed solution. Talc extra fine was dispersed and added to the formed solution to form a uniform suspension, which was then coated on sugar spheres 600-710 µm using a fluid bed coater. The functional coating suspension was prepared by dissolving Ethocel 45 cps (ethylcellulose; a release control polymer) in acetone and ethanol 96% mixture, and polyethylene glycol (PEG) 4000 was then dissolved in distilled water and added to the formed solution. The obtained suspension was coated on the drug-loaded pellets using a fluid bed coater.

TABLE 2

| Rasagiline mesylate ER coated pellets | | | |
|---|---|---|---|
| Ingredients | Mg/capsule | | |
| Cores - drug layered coated pellets | | | |
| Ethanol 96% | — | | |
| Distilled Water | — | | |
| Rasagiline mesylate | 1.0 | | |
| PVP K29/32 | 8.0 | | |
| Talc extra fine | 1.0 | | |
| Sugar spheres 600-710 µm | 90.0 | | |
| Total core weight | 100.0 | | |
| Functional coating (ER coating) | | | |
| | Example 4 15% ER | Example 5 22% ER | Example 6 28% ER |
| Acetone | — | — | — |
| Ethanol 96% | — | — | — |
| Distilled water | — | — | — |
| Ethocel 45 cps | 13.9 | 20.3 | 25.8 |
| PEG 4000 | 1.1 | 1.7 | 2.1 |
| Total | 115.0 | 122.0 | 127.9 |

Figure 4:
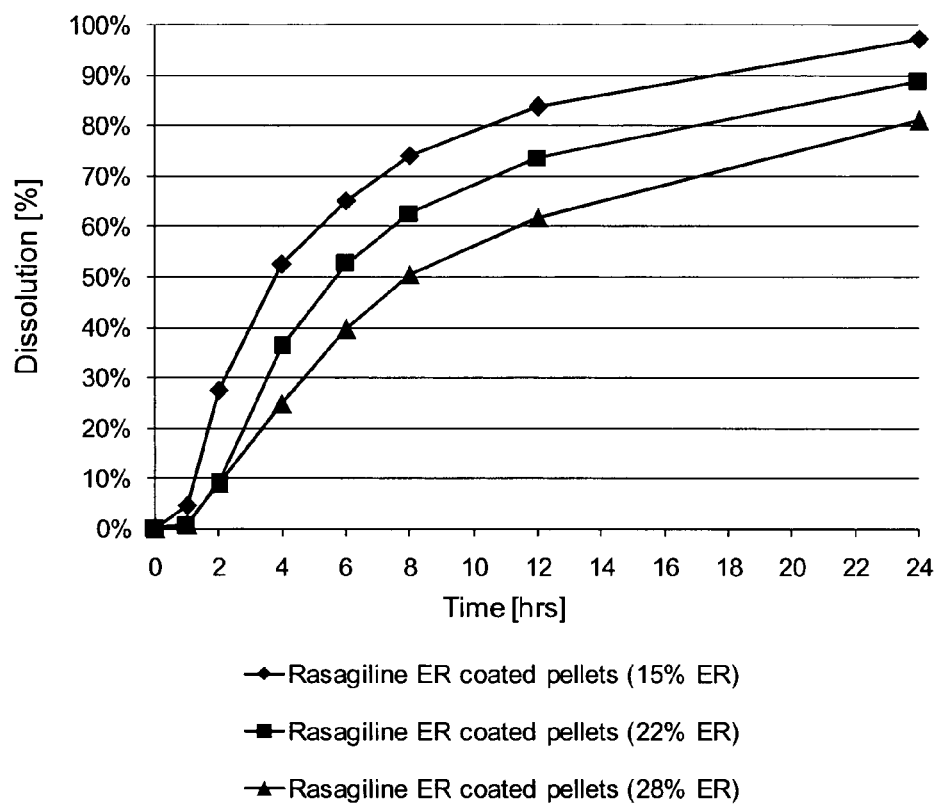
FIG. 4 shows in vitro dissolution data for the rasagiline mesylate (1.0 mg) extended release (ER) coated pellets of Examples 4-6 (15% ER, 22% ER and 28% ER, respectively) in IFS buffer.

The dissolution profiles of the various ER coated pellets were evaluated under the following conditions: USP (United States Pharmacopeia) Apparatus 1 was used to stir a dissolution medium (900 ml of intestinal fluid solution, IFS, pH 6.8) at a spindle rotation speed of 100 rpm and a temperature of 37° C. The dissolution profiles are shown in Table 3 and FIG. 4.

TABLE 3

In vitro dissolution data for the rasagiline mesylate ER coated pellets of Examples 4-6 in IFS buffer

| | % Dissolved | | |
|---|---|---|---|
| Time (hrs) | Example 4 | Example 5 | Example 6 |
| 0 | 0 | 0 | 0 |
| 1 | 5 | 1 | 1 |
| 2 | 28 | 9 | 9 |
| 4 | 53 | 36 | 25 |
| 6 | 65 | 53 | 40 |
| 8 | 74 | 53 | 51 |
| 12 | 84 | 74 | 62 |
| 24 | 97 | 89 | 81 |

Examples 7-8. Rasagiline Extended Release Coated Pellets with Sub Coating

Rasagiline mesylate ER pellets with sub coating having the composition shown in Table 4 were prepared. In particular, for the preparation of the drug layer, povidone (PVP K25) was dissolved in distilled water and ethanol 96% mixture, and rasagiline mesylate was then dissolved in the formed solution. Talc extra fine was dispersed and added to the formed solution to form a uniform suspension, which was then coated on sugar spheres 600-710 μm using a fluid bed coater. The sub coating solution was prepared by dissolving PVP K25 in distilled water and ethanol 96% mixture, and the obtained solution was then coated on the drug-loaded pellets using a fluid bed coater. The functional coating suspension was prepared by dissolving Ethocel 45 cps in acetone and ethanol 96% mixture, and PEG 3000 was then dissolved in distilled water and added to the formed solution. Talc extra fine was dispersed and added to the formed solution to form a uniform suspension, which was then coated on the sub coated pellets using a fluid bed coater. Dry mix of rasagiline ER pellets and Aerosil 200 were prepared using Tumbler Bin Blender.

Figure 5:
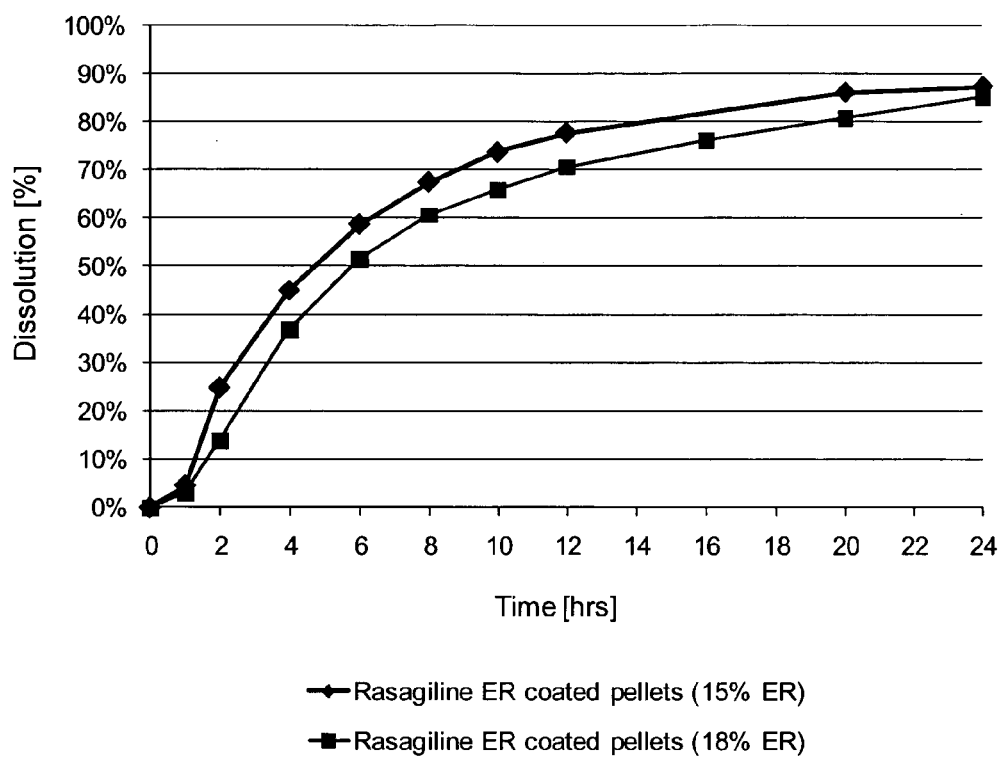
FIG. 5 shows in vitro dissolution data for the rasagiline mesylate (1.0 mg) extended release (ER) coated pellets with sub coating of Examples 7-8 (15% ER and 16% ER, respectively) in IFS buffer.
Figure 6:
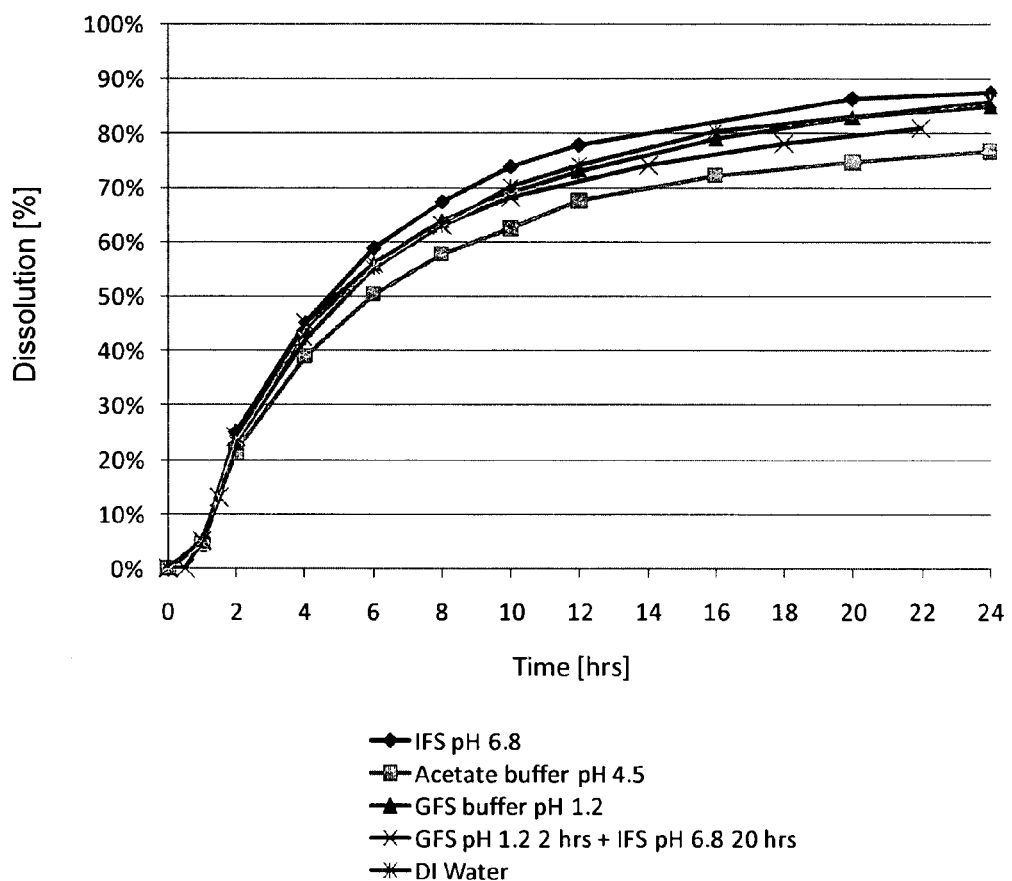
FIG. 6 shows in vitro dissolution data for the rasagiline mesylate (1.0 mg) extended release (ER) coated pellets with sub coating of Example 7 (15% ER) in (i) IFS buffer (pH 6.8), mimicking the conditions in the intestines; (ii) GFS buffer (pH 1.2), mimicking the conditions in an empty stomach; (iii) GFS buffer for 2 hrs, and then IFS buffer for additional 20 hrs; (iv) acetate buffer (pH 4.5), mimicking the conditions in a full stomach; and (v) distilled water (DI).
Figure 7:
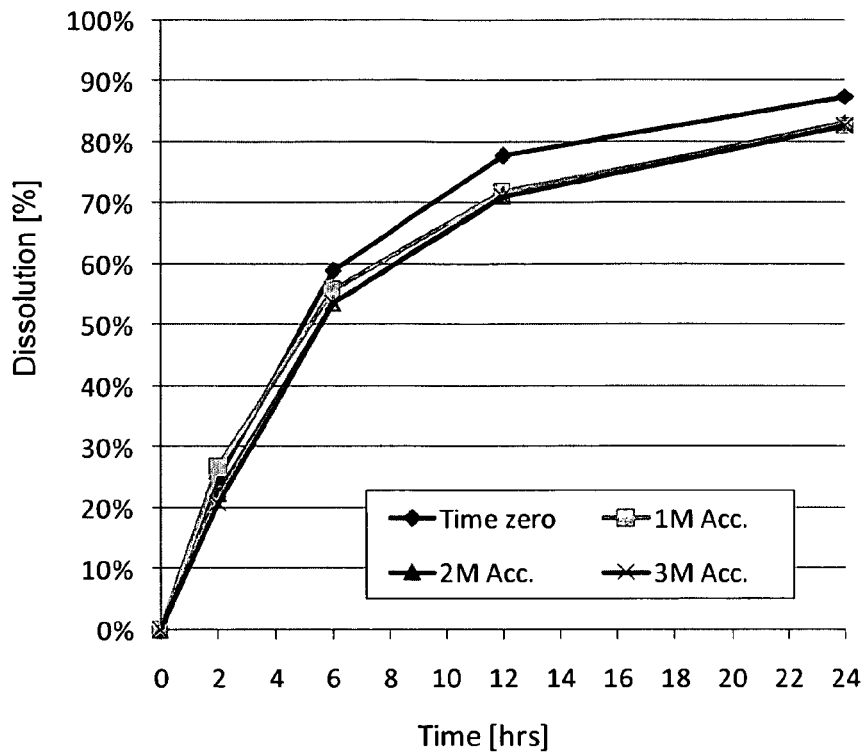
FIG. 7 shows in vitro stability data in IFS buffer for the rasagiline mesylate (1.0 mg) extended release (ER) coated pellets with sub coating of Example 7 (15% ER), at time zero (right after production), after 1 month at 40° C. and 75% humidity (1M Acc.), and after 2 and 3 months at 40° C. and 75% humidity (2M Acc. and 3M Acc., respectively).

The dissolution profiles of the various ER coated pellets were evaluated under the conditions used in Examples 4-6, and are shown in Table 5 and FIG. 5. In vitro dissolution data for the rasagiline mesylate ER coated pellets of Example 7 (15% ER) in (i) IFS buffer (pH 6.8), mimicking the conditions in the intestines; (ii) GFS (gastric fluid solution) buffer (pH 1.2), mimicking the conditions in an empty stomach; (iii) GFS buffer for 2 hrs, and then IFS buffer for additional 20 hrs; and (iv) acetate buffer (pH 4.5), mimicking the conditions in a full stomach, are shown in FIG. 6. In vitro stability data in IFS buffer for the same ER coated pellets at time zero (right after production), after 1 month in accelerated stability conditions (40° C., 75% humidity), and after 2 and 3 months at the same accelerated conditions are shown in FIG. 7.

TABLE 4

Rasagiline mesylate ER coated pellets with sub coating

| Ingredients | Mg/capsule |
|---|---|
| Cores - drug layered coated pellets | |
| Ethanol 96% | — |
| Distilled water | — |
| Rasagiline mesylate | 1.0 |
| PVP K25 | 8.0 |

TABLE 4-continued

Rasagiline mesylate ER coated pellets with sub coating

| | |
|---|---|
| Talc extra fine | 1.0 |
| Sugar spheres 600-710 μm | 90.0 |
| Total core weight | 100.0 |
| Cores - sub coated pellets | |
| Distilled water | — |
| Ethanol 96% | — |
| PVP K25 | 3.0 |
| Total SC core weight | 103.0 |
| Functional coating (ER coating) | |

| | Example 7<br>15% ER | Example 8<br>18% ER |
|---|---|---|
| Acetone | — | — |
| Ethanol 96% | — | — |
| Distilled water | — | — |
| Ethocel 45 cps | 13.90 | 16.68 |
| PEG 3000 | 0.78 | 0.93 |
| Talc extra fine | 0.78 | 0.93 |
| Total ER pellets weight | 118.45 | 121.54 |
| Dry mix | | |
| Aerosil 200 | 0.22 | 0.11 |
| Total | 118.67 | 121.65 |

TABLE 5

In vitro dissolution data for the rasagiline mesylate ER coated pellets of Examples 7-8 in IFS buffer

| | % Dissolved | |
|---|---|---|
| Time (hrs) | Example 7 | Example 8 |
| 0 | 0 | 0 |
| 1 | 5 | 3 |
| 2 | 25 | 14 |
| 4 | 45 | 37 |
| 6 | 59 | 52 |
| 8 | 67 | 61 |
| 10 | 74 | 66 |
| 12 | 78 | 71 |
| 16 | 79 | 76 |
| 20 | 86 | 81 |
| 24 | 87 | 85 |

Example 9. Rasagiline Extended Release Caps with Sub Coating

Figure 8:
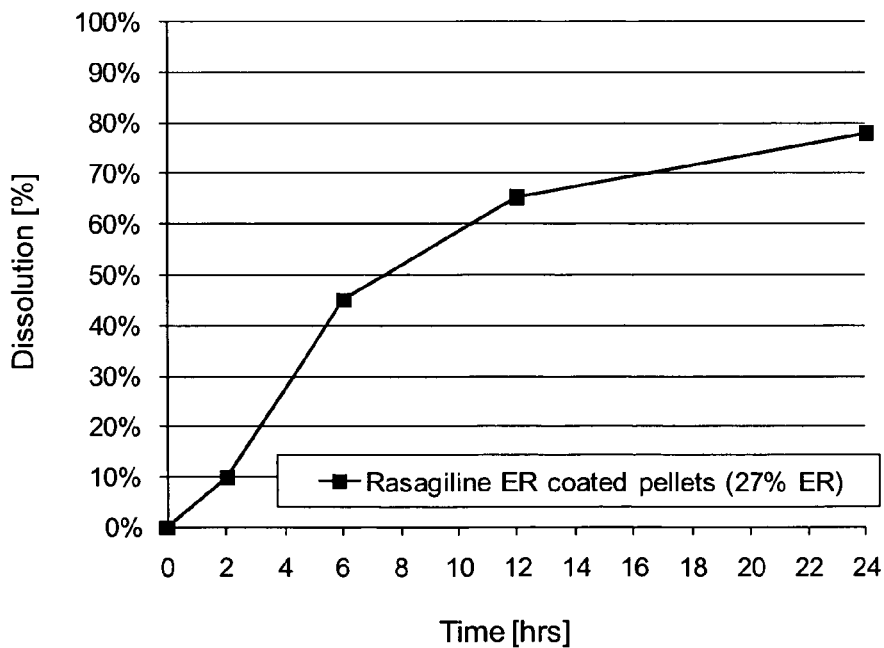
FIG. 8 shows in vitro dissolution data for the rasagiline mesylate extended release (ER) coated pellets with sub coating of Example 7 (27% ER) in IFS buffer.

Rasagiline mesylate ER pellets with sub coating having the composition shown in Table 6 were prepared as described in Examples 7-8; except for that silicon dioxide colloidal was used instead of Aerosil 200 for the preparation of the dry mix. The dissolution profile of these ER coated pellets prepared was evaluated under the conditions used in Examples 4-8, and is shown in Table 7 and FIG. 8.

TABLE 6

Rasagiline mesylate ER coated pellets with sub coating

| Ingredients | Mg/capsule<br>27% ER |
|---|---|
| Cores - drug layered coated pellets | |
| Ethanol 96% | — |
| Distilled water | — |

TABLE 6-continued

Rasagiline mesylate ER coated pellets with sub coating

| Ingredients | Mg/capsule 27% ER |
|---|---|
| Rasagiline mesylate | 1.59 |
| PVP K25 | 12.60 |
| Talc extra fine | 1.56 |
| Sugar spheres 600-710 μm | 141.73 |
| Total core weight | 157.48 |
| Cores - sub coated pellets | |
| Distilled water | — |
| Ethanol 96% | — |
| PVP K25 | 4.72 |
| Total SC core weight | 162.2 |
| Functional coating (ER coating) | |
| Acetone | — |
| Ethanol 96% | — |
| Distilled water | — |
| Ethocel 45 cps | 39.42 |
| PEG 3000 | 2.19 |
| Talc extra fine | 2.19 |
| Total ER pellets weight | 206.0 |
| Dry mix | |
| Silicon dioxide colloidal | 0.61 |
| Total | 206.61 |

TABLE 7

In vitro dissolution data for the rasagiline mesylate ER coated pellets of Example 9 in IFS buffer

| Time (hrs) | % Dissolved |
|---|---|
| 0 | 0 |
| 2 | 9.6 |
| 6 | 45.1 |
| 12 | 65.1 |
| 24 | 77.7 |

Example 10. Rasagiline Extended Release Coated Pellets with/without Sub Coating

Additional rasagiline mesylate ER pellets with or without sub coating, having the compositions shown in Tables 8-12, can be prepared according to the procedure described in Examples 4-9. Footnotes referred to in each one of the Tables included in this Example appear in the bottom of Table 16.

TABLE 8

Rasagiline mesylate 0.2 mg ER capsules (pH independent formulation)

| Ingredient | Range | Remarks |
|---|---|---|
| Active ingredient - Drug layering | | |
| Rasagiline mesylate 0.2 mg | 0.1-5.0%[1] | Drug substance/API |
| Hydroxypropyl cellulose (HPC) | 5-10% | Binder[3] |
| Talc | 2-5% | Glidant[4] |
| Sugar spheres/ Microcrystalline cellulose pellets | 50-80% | Cores |
| Purified water | | |
| Ethanol | | |

TABLE 8-continued

Rasagiline mesylate 0.2 mg ER capsules (pH independent formulation)

| Ingredient | Range | Remarks |
|---|---|---|
| Sub Coating (optional) | | |
| Hydroxypropylmethyl cellulose (HPMC) | 2-5% | Film-former polymer[5] |
| Purified water | | |
| Ethanol | | |
| Coating - Functional film coating | | |
| Ethyl cellulose (4-100 cps) | 5-25% | pH-independent polymer[6] |
| HPC | 1-12% | Pore-forming agent[7] |
| PEG 400 | 0.5-3% | Plasticizer[8] |
| Talc | 0.5-3% | Glidant[4] |
| Ethanol | | |
| Capsule shell | | |
| Gel caps/HPMC caps | | |

TABLE 9

Rasagiline mesylate 0.2 mg ER capsules (pulsatile drug delivery pH independent formulation)

| Ingredient | Range | Remarks |
|---|---|---|
| Active ingredient - Drug layering | | |
| Rasagiline mesylate 0.2 mg | 0.1-5.0%[1] | Drug substance/API |
| PVP K-30 (Povidone) | 3-8% | Binder[3] |
| Sodium chloride | 5-20% | Osmotic pressure agent[2] |
| Talc | 2-5% | Glidant[4] |
| Sugar spheres/ Microcrystalline cellulose pellets | 50-80% | Cores |
| Purified water | | |
| Ethanol | | |
| Coating - Functional film coating | | |
| Ethyl cellulose (4-100 cps) | 5-25% | pH-independent polymer[6] |
| PEG 400 | 0.5-3% | Plasticizer[8] |
| Talc | 0.5-3% | Glidant[4] |
| Ethanol | | |
| Purified water | | |
| Capsule shell | | |
| Gel caps/HPMC caps | | |

TABLE 10

Rasagiline mesylate 5 mg ER capsules (combination of pH-dependent and pH-independent polymers formulation)

| Ingredient | Range | Remarks |
|---|---|---|
| Active ingredient - Drug layering | | |
| Rasagiline mesylate 0.2 mg | 0.1-5.0%[1] | Drug substance/API |
| HPC | 5-10% | Binder[3] |
| Talc | 2-5% | Glidant[4] |
| Sugar spheres/ Microcrystalline cellulose pellets | 50-80% | Cores |
| Purified water | | |
| Ethanol | | |
| Sub coating (optional) | | |
| HPMC | 2-5% | Film-former polymer[5] |
| Purified water | | |
| Ethanol | | |

TABLE 10-continued

Rasagiline mesylate 5 mg ER capsules (combination of pH-dependent and pH-independent polymers formulation)

| Ingredient | Range | Remarks |
|---|---|---|
| Coating - Functional film coating | | |
| Ethyl cellulose | 5-25% | pH-independent polymer[6] |
| Eudragit ® L 55 | 1-12% | pH-dependent enteric coating polymer[9] |
| PEG 3000 | 1-12% | Pore-forming agent[7]; Plasticizer[8] |
| Dibutyl sebacate (DBS) | 0.5-3% | Plasticizer[8] |
| Talc | 0.5-3% | Glidant[4] |
| Ethanol | | |
| Capsule shell | | |
| Gel caps/HPMC caps | | |

TABLE 11

Rasagiline mesylate 5 mg multi-phase (IR + ER) release formulation*

| Ingredient | IR cores | ER cores | Remarks |
|---|---|---|---|
| Phase 1: Active ingredient - Drug layering | | | |
| Rasagiline mesylate 5 mg | 0.1-5.0%[1] | 0.1-5.0% | Drug substance/API |
| HPC | 5-10% | 5-10% | Binder[3] |
| Talc | 2-5% | 2-5% | Glidant[4] |
| Sugar spheres/Microcrystalline cellulose pellets | 60-90% | 50-80% | Cores |
| Purified water | | | |
| Ethanol | | | |
| Phase 2: Sub coating (optional) | | | |
| HPMC | 4-10% | 2-5% | Film-former polymer[5] |
| Purified water | | | |
| Ethanol | | | |
| Sub lot 1: Immediate release (IR) - proceed to dry mix (phase 4) | | | |
| Sub lot 2: ER coated pellets - proceed to phase 3 | | | |
| Phase 3: ER coating - functional film coating | | 5-95% of the batch | |
| Ethyl cellulose (4-100 cps) | NA | 5-25% | pH-independent polymer[6] |
| HPC | NA | 1-12% | Pore-forming agent[7] |
| PEG 400 | NA | 0.5-3% | Plasticizer[8] |
| DBS | NA | 0.5-3% | Plasticizer[8] |
| Talc | NA | 0.5-3% | Glidant[4] |
| Phase 4: Dry mix | | | |
| Rasagiline top coated pellets (eq. to 0.25-4.75 mg) - sub lot 1 - IR | | | |
| Rasagiline ER coated pellets (eq. to 0.25-4.75 mg) - sub lot 2 - ER | | | |
| Phase 5: Capsule shell | | | |
| Gel caps/HPMC caps | | | |

*Instead of two beads population, the multi-phase release particles can also be prepared as a uniform population: drug layer (0.25-4.75 mg) over sugar spheres or any other inert cores (phase 1) -> sub coat (phase 2) -> ER coat (phase 3) -> additional drug layer (0.25-4.75 mg) -> top coat (as in phase 2) -> capsule shell.

TABLE 12

Rasagiline mesylate 0.2 mg ER capsules (pH-dependent polymers; pH-independent polymers; or combination of pH-dependent and pH-independent polymers formulation)

| Ingredient | Range | Remarks |
|---|---|---|
| Active core (all ingredients are mixed together to create "wet mass", which is then extruded, spheronized, dried (FBD) and sieved before proceeding to sub coating phase. | | |
| Rasagiline mesylate 0.2 mg | 0.1-5.0%[1] | Drug substance/API |
| HPC | | Binder[3] |
| Starch | 20-40% | Filler[10] |
| Microcrystalline cellulose | 20-40% | Filler[10] |
| Purified water | | |
| Ethanol | | |
| Sub coating (optional) | | |
| HPMC | 2-5% | Film-former polymer[5] |
| Purified water | | |
| Ethanol | | |
| Coating - Functional film coating | | |
| Ethyl cellulose | 5-25% | pH-independent polymer[6] |
| PEG | 1-15% | Pore-forming agent[7]; Plasticizer[8] |
| Talc | 0.5-3% | Glidant[4] |
| Ethanol | | |
| Capsule shell | | |
| Gel caps/HPMC caps | | |

The rasagiline mesylate formulations described in Tables 2, 4 and 6, as well as those described in Tables 8-12 above may be compressed into tablet to formulate rasagiline ER coated tablets as well. For this purpose, rasagiline ER coated pellets are dry blended with additional excipients to create a homogenous blend, which is then compressed into tablets that are coated with a top/cosmetic/non functional coating layer (see, e.g., Table 13).

TABLE 13

Rasagiline mesylate 0.2 mg ER coated tablets

| Ingredient | Range | Remarks |
|---|---|---|
| Rasagiline 1 mg ER tablets | | |
| Rasagiline mesylate 0.2 mg ER coated pellets | 20-70% | From Tables 8-11 |
| Silicon dioxide | 1-10% | Glidant[4] |
| Microcrystalline cellulose (Avicel) | 20-70% | Filler/diluent[10]; disintegrant[11] |
| Magnesium stearate | 0.1-1.5% | Lubricant[12] |
| Rasagiline 1 mg ER coated tablets Cosmetic coat | | |
| Opadry (HPMC based coating material) | 3-5% | Mixed excipients for cosmetic/top/moisture barrier coating |
| Purified water | | |
| Ethanol | | |

Table 14 shows rasagiline 0.2 mg ER coated tablets formulation, prepared from wet granulation, which is then dried, milled, dry mixed, tableted, and finally coated with an ER coat.

TABLE 14

Rasagiline mesylate 0.2 mg ER coated tablets

| Ingredient | Range | Remarks |
|---|---|---|
| Rasagiline 1 mg tablets | | |
| Rasagiline mesylate 0.2 mg | 0.1-5.0%[1] | Drug substance |
| HPMC | 5-10% | Binder[3] |
| Starch pregelatinized | 30-50% | Filler/diluent[10]; disintegrant[11] |
| Silicon dioxide | 0.5-3% | Glidant[4] |
| Microcrystalline cellulose (Avicel) | 30-50% | Filler/diluent[10]; disintegrant[11] |
| Magnesium stearate | 0.1-1.5% | Lubricant[12] |
| Rasagiline 1 mg ER coated tablets | | |
| Ethyl cellulose | 5-15% | pH-independent polymer[6] |
| Opadry | 1-5% | Pore-forming agent[7] |
| Talc | 0.5-3% | Glidant[4] |
| Purified water | | |
| Ethanol | | |

Table 15 shows rasagiline 0.2 mg ER coated tablets formulation, prepared from wet granulation that includes the control release polymers, which is then dried, milled, dry mixed, tableted, and finally coated with a top coating.

TABLE 15

Rasagiline mesylate 0.2 mg ER coated tablets

| Ingredient | Range | Remarks |
|---|---|---|
| Rasagiline 1 mg tablets | | |
| Rasagiline mesylate 0.2 mg | 0.1-5.0%[1] | Drug substance |
| HPMC | 30-70% | Binder[3] |
| Starch | 10-40% | Filler/diluent[10]; disintegrant[11] |
| Ethyl cellulose | 10-40% | pH-independent polymer[6] |
| Magnesium stearate | 0.1-1.5% | Lubricant[12] |
| Rasagiline 1 mg ER coated tablets | | |
| Opadry | 3-5% | Mixed excipients for cosmetic/top/moisture barrier coating |
| Purified water | | |
| Ethanol | | |

Table 16 shows rasagiline 5 mg ER coated tablets formulation, prepared from wet granulation, which is then dried, milled, dry mixed, bi-layer tableted, and finally coated with a top coating.

TABLE 16

Rasagiline mesylate 5 mg ER coated tablets

| Ingredient | Range | Remarks |
|---|---|---|
| Rasagiline 0.25-4.75 mg IR layer | | |
| Rasagiline mesylate 5 mg | 0.1-5.0%[1] | Drug substance |
| Starch | 50-90% | Filler/diluent[10]; disintegrant[11] |
| Microcrystalline cellulose | 10-40% | Filler/diluent[10]; disintegrant[11] |
| PVP | 1-5% | Binder[3] |
| Magnesium stearate | 0.5-1.5% | Lubricant[12] |
| Rasagiline 0.25-4.75 mg ER layer | | |
| Rasagiline mesylate 5 mg | 0.1-5.0%[1] | Drug substance |
| Starch | 10-30% | Filler/diluent[10]; disintegrant[11] |
| Ethyl cellulose | 10-30% | pH-independent polymer[6] |
| HPMC | 40-80% | Binder[3] |
| Magnesium stearate | 0.5-1.5% | Lubricant[12] |
| Compressing bi-layer tablets using bi-layer tablet machine | | |
| Rasagiline 5 mg ER coated tablets | | |
| Opadry | 3-5% | Mixed excipients for cosmetic coat/top coat/moisture barrier coat |
| Purified water | | |
| Ethanol | | |

[1]The formulation may contain 0.2-5 mg of rasagiline mesylate
[2]Additional pH-dependent polymers instead or in addition to the osmotic pressure agent may be included to create the pulsatile drug release formulation.
[3]Alternative binders include, e.g., hydroxypropylmethyl cellulose (HPMC), povidone (PVP), microcrystalline cellulose, and combinations of said binders.
[4]Alternative glidants include, e.g., colloidal silicon dioxide, glyceryl monostearate, magnesium stearate, and combinations of said glidants.
[5]Alternative film-former polymers include, e.g., HPMC, PVP, microcrystalline cellulose, polyethylene glycol (PEG), and combinations of said film-former polymers.
[6]Alternative pH-independent polymers include, e.g., Surelease®, Eudragit® RL, Eudragit® RS, Eudragit® NE, and combinations of said polymers.
[7]Alternative pore-forming agents include, e.g., HPMC, PVP, PEG, and combinations of said pore-forming agents.
[8]Alternative plasticizers include, e.g., dibutyl sebacate/phthalate, triacetin, triethyl citrate, and combinations of said plasticizers.
[9]Alternative pH-dependent enteric coating polymers include, e.g., Eudragit® S, Kollicoat®, hydroxypropyl methylcellulose phthalate (HPMCP), and combinations of said agents.
[10]Alternative tablet fillers include, e.g., lactose, mannitol/Parteck®, Sorbitol, starch, and combinations of said tablet fillers.
[11]Alternative disintegrants include, e.g., sodium/calcium CMC, crospovidone, croscarmellose sodium hydroxypropyl cellulose low-substiuted, sodium bicarbonate, starch, sodium starch glycolate, and combinations of said disintegrants.
[12]Alternative lubricants include, e.g., glyceryl behenate, stearic acid, talc, zinc stearate, calcium stearate, and combinations of said lubricants.

Example 11. Absorption of Rasagiline from Various Parts of the Gastrointestinal Track Drugs are absorbed differently from various parts of the gastrointestinal track. In order to design a 24-hours sustained release product for oral administration, it is necessary that the drug be absorbed throughout the entire time, i.e., from all the parts of the gastrointestinal track. It is known that most drugs are well absorbed from the duodenum; however, many drugs are not well absorbed from the colon. Since a drug stays a significant amount of time in the colon before it is excreted from the body, it is important to evaluate its absorption from the colon in order to efficiently design the release profile.

In this study, rasagiline (1.5 mg/Kg) was administrated as an aqueous solution of 0.5 mg/ml via polyethylene cannula implanted one day before the pharmacokinetic experiment, to freely moving male Wistar rats. The cannulas were placed either in the colon, duodenum and jugular vein for colonic bolus, duodenal bolus and intravenous bolus administration, respectively. A single bolus dose administration to each compartment was done. In addition, a second indwelling cannula was placed in the right vein of each animal for systemic blood sampling. Blood samples (0.5 ml) were taken at 5 minutes pre-dose, 5, 15, 30, 50, 90, 150 and 200 minutes post-dose. To prevent dehydration, equal volumes of physiological solution were administered to the rats following each withdrawal of blood sample. Plasma was separated by centrifugation followed by analytical quantification of rasagiline and its major metabolite, 1-aminoindan, using LC-MS-MS triple quadropole. Non-compartmental pharmacokinetic analysis was performed using Excel software. The area under the curve (AUC) was calculated by non-compartmental analysis to the final measurable sample using the linear-log trapezoid method. The oral bioavailability (F) of rasagiline was calculated as the percentage ratio of: $AUC_{(deduneum)}/AUC_{(IV)}$ or $AUC_{(colon)}/AUC_{(IV)}$.

Figure 9:
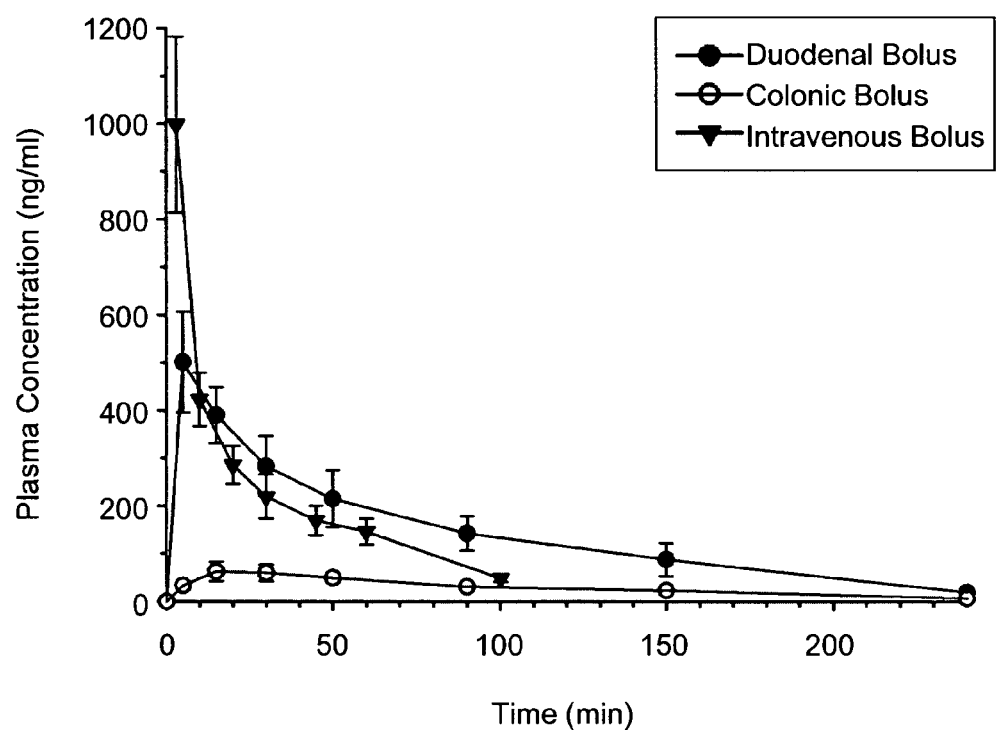
FIG. 9 shows the plasma concentration (ng/ml) vs. time plot of rasagiline administered by intravenous bolus, duodenal bolus or colonic bolus.

Table 17 and FIG. 9 show the differences in the maximum (or peak) plasma concentration (Cmax) and AUC between the duodenal and colonic administration groups (data are presented as mean±SE, n=4-5). In particular, parent $T_{1/2}$ was longer for the colonic and duodenal administration groups in comparison to $T_{1/2}$ after IV administration. Similar AUC values were calculated for the IV and duodenal dose suggesting a complete oral absorption. The AUC after colonic administration was approximately 28% of the IV dose AUC proving the feasibility of colonic absorption. According to these outcomes, the design of controlled release delivery system of rasagiline is feasible and practical.

TABLE 17

Phamacokintic parameters for rasagiline after IV, duodenal and colonic bolus (1.5 mg/Kg) administration

| Parameter | group* | | |
|---|---|---|---|
| | IV bolus* | Duodenal bolus* | Colonic bolus* |
| Tmax (min) | — | 7.5 ± 2.5 | 31.3 ± 7.2 |
| Cmax (ng/ml) | — | 505 ± 104 | 72.5 ± 21.3 |
| $T_{1/2}$(min) | 42.7 ± 5.5 | 79.5 ± 11.5 | 75 ± 5.5 |
| CL (ml/min/Kg) | 54.3 ± 7.1 | — | — |
| Vss (ml/Kg) | 2,404 ± 408 | — | — |
| AUC (hr * ng/ml) | 23,641 ± 3,481 | 24,181 ± 3,967 | 6,632 ± 1,362 |
| F (% of IV dose) | | ~100 | ~28 |

*Cmax—maximum plasma concentration; Tmax—time at which Cmax occurred; Vss—volume of distribution at steady state; Cl—clearance per Kg; F—oral bioavailability of rasagiline. Data are presented as mean ± SE (n = 4-5).

REFERENCES

Akao Y., Nakagawa Y., Maruyama W., Takahashi T., Naoi M., Apoptosis induced by an endogenous neurotoxin, N-methyl(R)salsolinol, is mediated by activation of caspase-3, *Neurosci. Lett.*, 1999, 267, 153-156

Akao Y., Maruyama W., Shimizu S., Yi H., Nakagawa Y., Shamoto-Nagai M., Youdim M. B. H., Tsujimoto Y., Naoi M., Mitochondrial permeability transition mediates apoptosis induced by N-methyl(R)salsolinol, an endogenous neurotoxin, and is inhibited by Bcl-2 and Rasagiline, N-Propargyl-1(R)-aminoindan, *J. Neurochem.*, 2002a, 82, 913-923

Akao Y., Maruyama W., Yi H., Shamoto-Nagai M., Youdim M. B. H., Naoi M., An anti-Parkinson's disease drug, N-propargyl-1(R)-aminoindan (rasagiline), enhances expression of anti-apoptotic Bcl-2 in human dopaminergic SH-SYSY cells, *Neurosci. Lett.*, 2002b, 326, 105-108

Bar-Am O., Amit T., Youdim M. B., Aminoindan and hydroxyaminoindan, metabolites of rasagiline and ladostigil, respectively, exert neuroprotective properties in vitro, *J. Neurochem.*, 2007, 103(2), 500-508

Bar-Am O., Weinreb O., Amit T., Youdim M. B., The neuroprotective mechanism of 1-(R)-aminoindan, the major metabolite of the anti-parkinsonian drug rasagiline, *J. Neurochem.*, 2010, 112, 1131-1137

Durden D. A., Dyck L. E., Davis B. A., Liu Y. D., Boulton A. A., Metabolism and pharmacokinetics, in the rat, of (R)—N-(2-heptyl)methyl-propargylamine (R-2HMP), a new potent monoamine oxidase inhibitor and antiapoptotic agent, *Drug Metab Dispos.*, 2000, 28, 147-154

Grossberg G., Desai A., Review of rivastigmine and its clinical applications in Alzheimer's disease and related disorders, *Expert Opin. Pharmacother.*, 2000, 2, 653-666

Maruyama W., Boulton A. A., Davis B. A., Dostert P., Naoi M., Enantio-specific induction of apoptosis by an endogenous neurotoxin, N-methyl(R)salsolinol, in dopaminergic SH-SY5Y cells: suppression of apoptosis by N-(2-heptyl)-N-methylpropargylamine, *J. Neural Transm.*, 2001a, 108, 11-24

Maruyama W., Akao Y., Youdim M. B. H., Boulton A. A., Davis B. A., Naoi M., Transfection-enforced Bcl-2 overexpression and an anti-Parkinson drug, rasagiline, prevent nuclear accumulation of glyceraldehyde-3 phosphate dehydrogenase induced by an endogenous dopaminergic neurotoxin, N-methyl(R)salsolinol, *J. Neurochem.*, 2001b, 78, 727-735

Maruyama W., Takahashi T., Youdim, M. B. H., Naoi M., The anti-Parkinson drug, rasagiline, prevents apoptotic DNA damage induced by peroxynitrite in human dopaminergic neuroblastoma SH-SY5Y cells, *J. Neural Transm.*, 2002, 109, 467-481

Tazik S., Johnson S., Lu D., Johnson C., Youdim M. B., Stockmeier C. A., Ou X. M., Comparative neuroprotective effects of rasagiline and aminoindan with selegiline on dexamethasone-induced brain cell apoptosis, *Neurotoxicity Research*, 2009, 15, 284-290

Tatton W. G., Chalmers-Redman R. M., Ju W. J., Mammen M., Carlile G. W., Pong A. W., Tatton N. A., Propargylamines induce antiapoptotic new protein synthesis in serum- and nerve growth factor (NGF)-withdrawn, NGF-differentiated PC-12 cells, *J Pharmacol Exp Ther.*, 2002, 301, 753-764

Tatton W. G., Greenwood C. E., Rescue of dying neurons: a new action for deprenyl in MPTP parkinsonism, *J Neurosci Res.*, 1991, 30, 666-672

Tatton W. G., Selegiline can mediate neuronal rescue rather than neuronal protection, *Movement Disorders* 8 (Supp. 1), 1993, S20-S30

Weinreb O., Amit T., Bar-Am O., Yousim M. B., Rasagiline: a novel anti-Parkinsonian monoamine oxidase-B inhibitor with neuroprotective activity, *Prog Neurobiol.*, 2010, 92(3), 330-344

Weinstock M., Selectivity of cholinesterase inhibition: Clinical implications for the treatment of Alzheimer's disease, *CNS Drugs*, 1999, 12, 307-323

Yogev-Falach M., Amit T., Bar-Am O., Sagi Y., Weinstock M., Youdim M. B. H., The involvement of mitogen-activated protein (MAP) kinase in the regulation of amyloid precursor protein processing by novel cholinesterase inhibitors derived from rasagiline, *FASEB J.*, 2002, 16, 1674-1676

Youdim M. B. H., Weinstock M., ovel neuroprotective anti-Alzheimer drugs with antidepressant activity derived from the anti-Parkinson drug, rasagiline, *Mechanisms of Ageing & Developments*, 2002a, 123, 1081-1086

Youdim M. B. H., Gross A., Finberg J. P. M., Rasagiline [N-Propargyl-1R(+)-aminoindan], a selective and potent inhibitor of mitochondrial monoamine oxidase B, *Br. J. Pharmacol.*, 2001a, 132, 500-506

Youdim M. B. H., Wadia A., Tatton N. A., Weinstock M., The anti-Parkinson drug rasagiline and its cholinesterase inhibitor derivatives exert neuroprotection unrelated to MAO inhibition in cell culture and in vivo, *Ann N Y Acad Sci*, 2001b, 939, 450-458

Zimmermann K, Waldmeier P. C., Tatton W. G., Dibenzoxepines as treatments for neurodegenerative diseases, *Pure Appl Chem*, 1999, 71, 2039-2046

The invention claimed is:

1. An extended release oral pharmaceutical composition, comprising an active agent comprising rasagiline, or a pharmaceutically acceptable salt thereof, wherein the composition contains 0.2-2.0 mg of said active agent and is formulated such that the composition has a dissolution profile in USP Apparatus 1 (basket) at 50-150 rpm in pH value of up to 7.4 at 37° C., that 30-70% of said active agent is released over the first six hours.

2. The pharmaceutical composition of claim 1, wherein said pharmaceutically acceptable salt is selected from the group consisting of the mesylate salt, the esylate salt, the tosylate salt, the sulfate salt, the sulfonate salt, the phosphate salt, the carboxylate salt, the maleate salt, the fumarate salt, the tartrate salt, the benzoate salt, the acetate salt, the hydrochloride salt, and the hydrobromide salt.

3. The pharmaceutical composition of claim 1, in the form of a coated pellet, a monolithic matrix, a tablet, a capsule or a sachet.

4. The pharmaceutical composition of claim 1, formulated so as to have the following dissolution profile in USP Apparatus 1 (basket) at 50-150 rpm in pH value of up to 7.4 at 37° C.:

| Time (hours) | Average % active agent released |
| --- | --- |
| 2 | <30 |
| 6 | 30-70 |
| 12 | 50-85 |
| 24 | >70 |

5. The pharmaceutical composition of claim 1, comprising a plurality of extended-release pellets, each comprising:
 (i) an inert pellet core;
 (ii) a layer of said active agent coating said pellet core; and
 (iii) an extended-release layer surrounding said layer of active agent, said extended-release layer comprising a pH-independent polymer.

6. The pharmaceutical composition of claim 5, wherein each one of said extended release pellets further includes an isolating/protecting sub-coating layer between said drug layer and said extended-release layer.

7. The pharmaceutical composition of claim 5, wherein:
 (i) said layer of active agent comprises said active agent suitably admixed with a binder and/or a film-former polymer, and further admixed with a glidant, wherein said binder, when present, is a polyvinyl pyrrolidone (PVP), hydroxypropylmethyl cellulose (HPMC), hydroxypropyl cellulose (HPC), microcrystalline cellulose, or a combination thereof; said film-former polymer, when present, is PVP, HPMC, HPC, microcrystalline cellulose, or a combination thereof; and said glidant is talc, colloidal silicon dioxide, glyceryl monostearate, or a combination thereof; and/or
 (ii) said pH-independent polymer is ethyl cellulose, aqueous ethylcellulose dispersion, copolymers of acrylic and methacrylic acid esters, or a combination thereof.

8. The pharmaceutical composition of claim 5, wherein said extended-release pellet comprises:
 (i) an inert pellet core; a drug layer comprising said active agent admixed with PVP as a film-former polymer/binder and with talc extra fine as a glidant; and an extended-release (ER) coating layer comprising ethylcellulose as a pH-independent polymer, and PEG as a pore-forming agent, wherein the amount of said film-former polymer/binder is up to 90% by weight of the entire drug layer, or from about 0.5% to about 20% by weight of the entire pellet; the amount of said glidant is up to 30% by weight of the entire drug layer, or from about 0.1% to about 10% by weight of the entire pellet; the amount of said pH-independent polymer is from about 50% to about 90% by weight of the entire ER coating layer, or from about 10% to about 30% by weight of the entire pellet; and the amount of said pore-forming agent is from about 1% to about 20% by weight of the entire ER coating layer, or from about 0.1% to about 10% by weight of the entire pellet; or
 (ii) an inert pellet core; a drug layer comprising said active agent admixed with PVP as a film-former polymer/binder and with talc extra fine as a glidant; an isolating/protecting sub-coating layer comprising PVP as a film-former polymer; and an ER coating layer comprising ethylcellulose as a pH-independent polymer, PEG as a pore-forming agent, and talc extra fine as a glidant, wherein the amount of said film-former polymer/binder in said drug layer is up to 90% by weight of the entire drug layer, or from about 0.5% to about 20% by weight of the entire pellet; the amount of said glidant in said drug layer is up to 30% by weight of the entire drug layer, or from about 0.1% to about 10% by weight of the entire pellet; the amount of said film-former polymer in said sub-coating layer is up to 100% by weight of the entire sub-coating layer, or from about 0.5% to about 20% by weight of the entire pellet; the amount of said pH-independent polymer is from about 50% to about 90% by weight of the entire ER coating layer, or from about 10% to about 30% by weight of the entire pellet; the amount of said pore-forming agent is from about 1% to about 20% by weight of the entire ER coating layer, or from about 0.1% to about 10% by weight of the entire pellet; and the amount of said glidant in said ER coating layer is from about 0.1% to about 20% by weight of the entire ER coating layer, or from about 0.1% to about 10%, by weight of the entire pellet.

9. The pharmaceutical composition of claim 5, wherein said extended-release pellets are blended with one or more suitable excipients and either filled into a capsule or compressed into a tablet.

10. A method for treatment of a neurodegenerative disease or an injury to the nervous system in an individual in need thereof, comprising administering to said individual a daily dose of the pharmaceutical composition of claim 1.

11. The method of claim 10, wherein said neurodegenerative disease is Parkinson's disease or Alzheimer's disease, and said injury to the nervous system is acute brain damage, or traumatic brain injury.

12. A method for preparing the pharmaceutical composition according to claim 5, wherein each of said pellets are prepared by a method comprising the steps of:
 (i) dissolving said active agent in a suitable solvent system to prepare a uniform suspension;
 (ii) applying a coat of the suspension obtained in (i) to inert pellets;
 (iii) optionally coating the active agent-loaded pellets obtained in (ii) with an insulating/protecting sub-coating layer;
 (iv) coating the pellets obtained in (ii) or, if present, (iii) with said extended-release coating layer.

13. The method of claim 12, further including the step of filling said extended-release pellets into capsules or compressing said pellets into tablets.

14. A method for treatment of a neurodegenerative disease or an injury to the nervous system in an individual in need thereof, comprising administering to said individual a daily dose of the pharmaceutical composition of claim 5.

15. The method of claim 14, wherein said neurodegenerative disease is Parkinson's disease or Alzheimer's disease, and said injury to the nervous system is acute brain damage, or traumatic brain injury.

16. The pharmaceutical composition of claim 5, formulated so as to have the following dissolution profile in USP Apparatus 1 (basket) at 50-150 rpm in pH value of up to 7.4 at 37° C.:

| Time (hours) | Average % active agent released |
|---|---|
| 2 | <30 |
| 6 | 30-70 |
| 12 | 50-85 |
| 24 | >70 |

17. The pharmaceutical composition of claim 6, wherein said sub-coating layer comprises a film-former polymer.

18. The pharmaceutical composition of claim 5, wherein said extended-release layer further comprises a pore-forming agent.

19. The pharmaceutical composition of claim 18, wherein said pore-forming agent is PVP, PEG, HPMC, HPC, methylcellulose, 1,2-propylene glycol, lactose, sucrose, talc, or a combination thereof.

20. The pharmaceutical composition of claim 5, wherein said extended-release layer comprises said pH-independent polymer, a hydrophilic release modulator polymer and a hydrophobic or hydrophilic plasticizer and/or a glidant.

21. The pharmaceutical composition of claim 20, wherein said hydrophilic release modulator polymer is HPMC, HPC, PVP, PEG, or a combination thereof; said plasticizer, when present, is dibutyl sebacate, dibutyl phthalate, a citrate ester, propylene glycol, a low molecular weight poly(alkylene oxide), or a combination thereof; and said glidant, when present, is talc, colloidal silicon dioxide, glyceryl monostearate, or a combination thereof.

22. The pharmaceutical composition of claim 5, wherein said extended-release layer comprises a mixture of said pH-independent polymer and a pH-dependent enteric-coating polymer, formulated so as to have close to a zero order in vitro release characteristic at pH value of up to pH 7.4.

23. The pharmaceutical composition of claim 22, wherein said pH-dependent enteric-coating polymer is poly(methacrylicacid, methylmethacrylate), 1:2, poly (methacrylicacid, ethylacrylate), 1:1, poly(methacrylicacid, ethylacrylate), 1:1, hydroxypropylmethyl cellulose phthalate (HPMCP), alginates, carboxymethylcellulose, or a combination thereof.

24. The pharmaceutical composition of claim 4, formulated so as to have the following dissolution profile in USP Apparatus 1 (basket) at 50-150 rpm in pH value of up to 7.4 at 37° C.:

| Time (hours) | Average % active agent released |
|---|---|
| 2 | <30 |
| 6 | 30-60 |
| 12 | 50-70 |
| 24 | >70. |

25. The pharmaceutical composition of claim 16, formulated so as to have the following dissolution profile in USP Apparatus 1 (basket) at 50-150 rpm in pH value of up to 7.4 at 37° C.:

| Time (hours) | Average % active agent released |
|---|---|
| 2 | <30 |
| 6 | 30-60 |
| 12 | 50-70 |
| 24 | >70. |

* * * * *